US012761213B2

(12) United States Patent
Hering et al.

(10) Patent No.: US 12,761,213 B2
(45) Date of Patent: Oct. 13, 2026

(54) BIOMARKER FOR TRANSPLANTATION TOLERANCE INDUCED BY APOPTOTIC DONOR LEUKOCYTES

(71) Applicant: Regents of the University of Minnesota, Minneapolis, MN (US)

(72) Inventors: Bernhard J. Hering, Minneapolis, MN (US); Sabarinathan Ramachandran, Minneapolis, MN (US); Amar Singh, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1129 days.

(21) Appl. No.: 17/604,314

(22) PCT Filed: Apr. 16, 2020

(86) PCT No.: PCT/US2020/028575
§ 371 (c)(1),
(2) Date: Oct. 15, 2021

(87) PCT Pub. No.: WO2020/214849
PCT Pub. Date: Oct. 22, 2020

(65) Prior Publication Data
US 2022/0214333 A1 Jul. 7, 2022

Related U.S. Application Data

(60) Provisional application No. 62/834,798, filed on Apr. 16, 2019.

(51) Int. Cl.
*G01N 33/50* (2006.01)
*G01N 33/569* (2006.01)

(52) U.S. Cl.
CPC ... *G01N 33/5094* (2013.01); *G01N 33/56972* (2013.01); *G01N 2800/245* (2013.01); *G01N 2800/52* (2013.01)

(58) Field of Classification Search
CPC ......... G01N 33/56972; G01N 33/5094; G01N 2800/52; G01N 2800/245
USPC ........................................................ 436/63
See application file for complete search history.

(56) References Cited

U.S. PATENT DOCUMENTS 5,837,832 A 11/1998 Chee et al.
7,744,863 B1 * 6/2010 Hall ................. A61K 39/39541 424/156.1
8,734,786 B2 5/2014 Miller et al.
2003/0059426 A1 3/2003 Edelson
2003/0133914 A1 7/2003 Edelson et al.
2006/0240024 A1 10/2006 Pardoll et al.
2007/0098686 A1 * 5/2007 Peritt ..................... A61K 40/42 514/291
2007/0202085 A1 8/2007 Hu et al.
2010/0209409 A1 8/2010 Edelson et al.
2011/0064709 A1 * 3/2011 Miller .................... A61K 35/38 424/93.71
2012/0329668 A1 * 12/2012 Sarwal ................. C12Q 1/6888 435/6.12
2014/0057315 A1 2/2014 Sindhi et al.
2015/0132272 A1 * 5/2015 Flavell ................. A61K 40/416 435/325
2015/0283218 A1 * 10/2015 Shea ...................... A61K 39/00 424/499
2016/0165861 A1 * 6/2016 Hering ................. A61K 31/436 800/24
2016/0169890 A1 6/2016 Sykes et al.
2017/0038395 A1 2/2017 Jarvis et al.
2017/0349950 A1 12/2017 Regev et al.
2018/0050092 A1 2/2018 Gregori et al.
2018/0360884 A1 12/2018 Adusumilli
2019/0263931 A1 * 8/2019 Rothstein ................ A61P 37/06
2022/0112280 A1 * 4/2022 Hering ............... A61K 39/3955

FOREIGN PATENT DOCUMENTS

WO 2010104617 A2 9/2010
WO 2013192215 A1 12/2013
WO 2020082051 A1 4/2020

OTHER PUBLICATIONS

Akl, A et al, Transplant Immunology 2005, 14, 225-230. (Year: 2005).*
Jiang, S. et al., Human Immunology 2006, 67, 765-776. (Year: 2006).*
Carpentier, A. et al., American Journal of Transplantation 2009, 9, 2102-2112. (Year: 2009).*
Charbonnier, L.-M et al, Journal of Autoimmunity 2010, 34, 390-399. (Year: 2010).*
Newell, K. A. et al, Current Opinion in Immunology 2011, 23, 655-659. (Year: 2011).*
Bacchetta, R. et al, Frontiers in Immunology 2014, 5, article 16, 14 pages. (Year: 2014).*
Andreani, M. et al, Chimerism 20144, 5, 75-79. (Year: 2014).*
Zeng, H. et al, Cellular & Molecular Immunology 2015, 12, 566-571. (Year: 2015).*
Petrelli, A. et al, Transplantation 2015, 99, 1582-1589. (Year: 2015).*
White, A. M. et al, Frontiers in Immunity 2016, 7, article 355, 7 pages. (Year: 2016).*
Mfarrej, B. et al, Journal of Translational Medicine2017, 15, article 40, 12 pages with 9 pages of additional files. (Year: 2017).*

(Continued)

*Primary Examiner* — Arlen Soderquist
(74) *Attorney, Agent, or Firm* — Viksnins Harris Padys Malen LLP

(57) ABSTRACT

In certain embodiments, the present invention provides methods of identifying and treating a transplant recipient patient having transplantation tolerance induced by apoptotic donor leukocytes infused under cover of transient immunotherapy.

19 Claims, 6 Drawing Sheets

(56) References Cited

OTHER PUBLICATIONS

Gregori, S. et al, Frontiers in Immunity 2018, 9, article 233, 8 pages. (Year: 2018).*
Kim, J. et al, Journal of Investigative Dermatology 2018, 138, 2669-2672 with 8 pages of supplementary material. (Year: 2018).*
Battaglia, M. et al, Diabetes 2006, 55, 40-49. (Year: 2006).*
Peche, H. et al, American Journal of Transplantation 2006, 6, 1541-1550. (Year: 2006).*
Gandhi, R. et al, Nature Immunity 2010, 11, 846-854. (Year: 2010).*
Chen, G. et al, American Journal of Transplantation 2012, 12, 2920-2929. (Year: 2012).*
Li, X. et al, PLOS One 2012, 7, paper e44045, 12 pages. (Year: 2012).*
Bryant, J. et al, Biomaterials 2014, 35, 8887-8894. (Year: 2014).*
Xu, H. et al, American Journal of Transplantation 2016, 16, 550-564. (Year: 2016).*
Kang, H. K. et al, Transplantation 2017, 101, 1801-1810. (Year: 2017).*
Chhabra, A , et al., "HSCT-Based Approaches for Tolerance Induction in Renal Transplant", Transplantation 101, 2682-2690 (2017).
Luo, X. , et al., "ECOi-fixed allogeneic splenocytes induce donor-specific tolerance for long-term survival of islet transplants via two distinct mechanisms", National Academy of Sciences 105(38), 14527-14532 (2008).
Mccarthy, D. P. , et al., "Tempering Allorecognition to Induce Transplant Tolerance With Chemically Modified Apoptotic Donor Cells", Am. J. Transplant 15(6), 1475-1483 (2015).
Mougel, F. , et al., "Intravenous infusion of donor apoptotic leukocytes before transplantation delays allogeneic islet graft rejection through regulatory T cells", Diabetes & Metabolism 38, 531-537 (2012).
Gagliani, N , et al., "Coexpression of CD49b and LAG-3 identifies human and mouse T regulatory type 1 cells", Nature Medicine 19 (6), 739-746, Online Methods 2 pages (2013).
Gagliani, N , et al., "Transplant Tolerance to Pancreatic Islets Is Initiated in the Graft and Sustained in the Spleen", American Journal of Transplantation 13, 1963-1975 (2013).
Patent Cooperation Treaty , International Search Report and Written Opinion for PCT/US2020/028575, 10 pages, dated Jul. 21, 2020.
Roncarolo, M , et al., "The Biology of T Regulatory Type 1 Cells and Their Therapeutic Application in Immune-Mediated Diseases", Immunity 49, 1004-1019 (2018).
Roncarolo, M , et al., "Tr1 Cells and the Counter-Regulation of Immunity: Natural Mechanisms and Therapeutic Applications", Current Topics in Microbiology and Immunology 380, DOI: 10.1007/978-3-662-43492-5_3, 39-68 (2014).
Safley, S , et al., "Abstract O.5.6—Mechanisms of destruction of microencapsulated adult porcine islets transplanted intraperitoneally in streptozotocin-diabetic non-human primates", Xenotransplanation 24, e12328, 38-39, 108 pages (2017).
Safley, S , et al., "Mechanisms of destruction of microencapsulated adult porcine islets transplanted intraperitoneally in streptozotocin-diabetic non-human primates", IXA 2017—Abstracts of the 14th Congress of the International Kenotransplantation Association, Baltimore, USA, 3 pages (Sep. 11, 2017).
Sayitoglu, E , et al., "The Yin and Yang of Type 1 Regulatory T Cells: From Discovery to Clinical Application", Front. Immunol. 12, (693105), 1-9 (2021).
Singh, A , et al., "Long-term tolerance of islet allografts in nonhuman primates induced by apoptotic donor leukocytes", Nature Communications 10 (3495), 16 pages (2019).
Uchtenhagen, H , et al., "Efficient ex vivo analysis of CD4þ T-cell responses using combinatorial HLA class II tetramer staining", Nature Communications 7 (12614), 12 pages (2016).

* cited by examiner

Figure 1C Transcription Profile of Tr1 cells
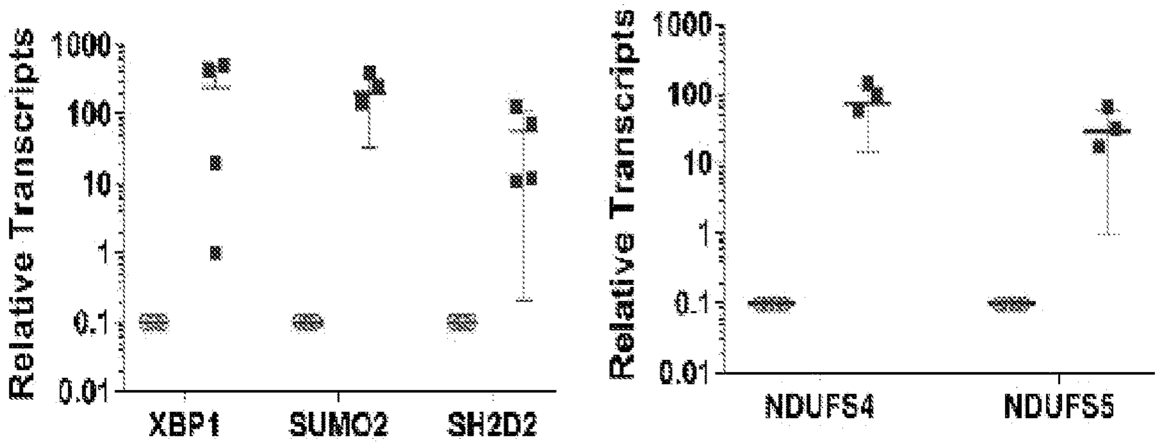
Figure 2. Increased Frequency of Tr1 cells in Tolerant Animals
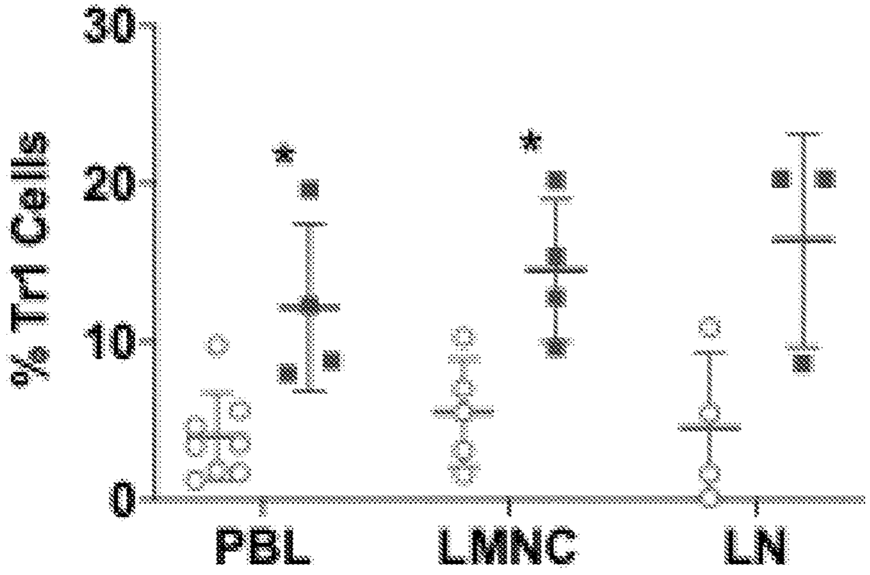

Figure 3. Depletion of Tr1 cells in Tolerant Animals Restores Donor-specific Proliferation
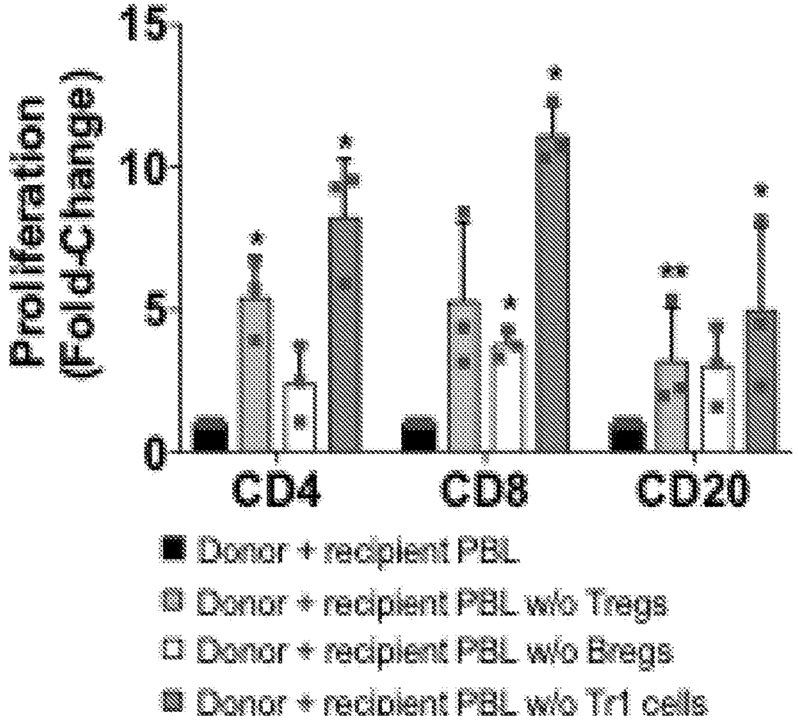
Figure 4.
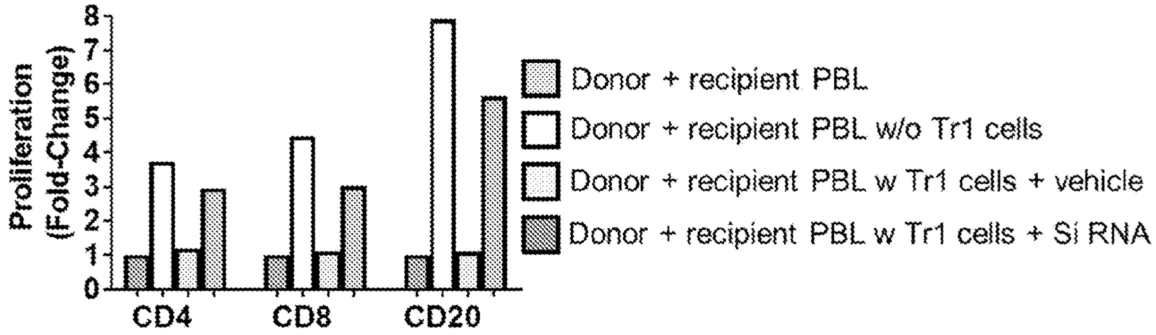

Figure 5. Increased Frequency of Tetramer+ Donor-specific Tr1 cells in Tolerant Animals
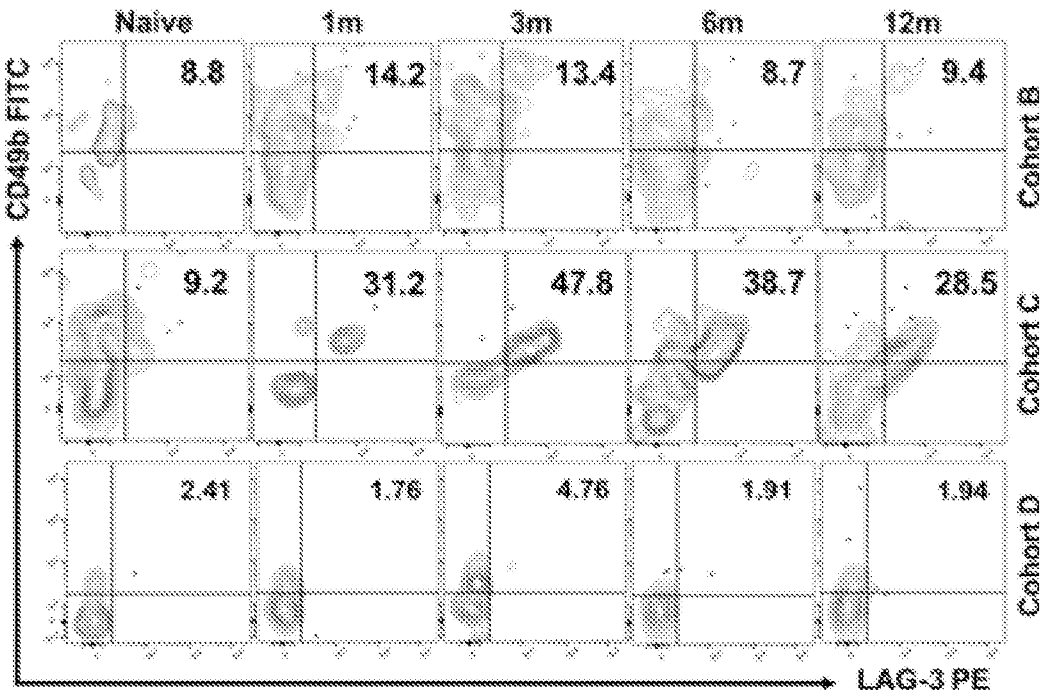

BIOMARKER FOR TRANSPLANTATION TOLERANCE INDUCED BY APOPTOTIC DONOR LEUKOCYTES

RELATED APPLICATION

This application claims priority to U.S. Provisional Application No. 62/834,798 that was filed on Apr. 16, 2019. The entire content of the application referenced above is herein incorporated by reference in its entirety.

STATEMENT REGARDING FEDERALLY SPONSORED RESEARCH

This invention was made with government support under AI102463 awarded by National Institutes of Health. The government has certain rights in the invention.

BACKGROUND OF THE INVENTION

For many patients with end-stage organ failure, a transplant has become the most effective treatment option. Current immunosuppressive regimens effectively prevent acute rejection; however, their significant morbidity and their lack of efficacy in preventing chronic rejection remain serious problems. A growing population of chronically immunosuppressed transplant recipients continue to struggle with such problems, which adversely affect their survival. Inducing tolerance to allografts would remove the need for maintenance immunotherapy and improve long-term allograft survival; yet, despite its first demonstration in small animal models more than 65 years ago and its clinical significance, tolerance has been achieved in only a very few patients through mixed hematopoietic chimerism, which requires extensive conditioning therapy. Likewise, in translational models in monkeys, only mixed chimerism has nearly consistently induced tolerance to same-donor kidney allografts.

In nonhuman primate studies, an apoptotic donor leukocyte regimen was consistently effective and required much less intense, short-term immunotherapy. Because of its efficacy and its very favorable safety profile, this regimen is the first clinically translatable, nonchimeric transplantation tolerance regimen. A biomarker for monitoring the induction, maintenance, and loss of transplant tolerance in human recipients is required.

SUMMARY OF THE INVENTION

This present invention identifies a biomarker for monitoring the induction, maintenance, and loss of tolerance in human recipients of solid organ, tissue and cellular allotransplants.

In certain embodiments, the present invention provides A method of identifying a transplant recipient patient having transplantation tolerance induced by donor antigen administered under cover of transient immunotherapy, comprising: (a) assaying a first blood sample from the patient to detect a baseline frequency of target cells, wherein the first blood sample is obtained pre-tolerization, pre-transplant, and pre-initiation of transient immunotherapy, (b) assaying a second blood sample from the patient to detect a post-procedure frequency of target cells, wherein the second sample is obtained post-tolerization, post-transplant, and post-initiation of transient immunotherapy; and (c) identifying the patient as having transplantation tolerance/immune acceptance induced by donor antigens when the post-procedure frequency is at least 2-fold greater than the baseline frequency, wherein the target cells are T regulatory Type 1 (Tr1) cells having markers CD49b+, LAG-3+, CD4+. In certain embodiments, the transplant recipient patient having transplantation tolerance induced by donor antigen administered under cover of transient immunotherapy has transplantation tolerance maintained. In certain embodiments, the donor antigens are apoptotic donor leukocytes (ADLs), donor-specific transfusion (DST) nanoparticles conjugated with donor peptides or encapsulating donor peptides, and/or apoptotic recipient leukocytes conjugated with donor peptides. In certain embodiments, the target cells are T regulatory Type 1 (Tr1) cells having markers CD49b+, LAG-3+, CD4+, have indirect specificity for at least one mismatched donor MHC class I peptide, have a transcriptomic signature indicative of antigen-specific signaling, and have a transcriptomic signature indicative of an activated state.

In certain embodiments, the transplant recipient patient has transplantation tolerance maintained. In certain embodiments, the transplant recipient patient had immune tolerance induced but failed. In certain embodiments, immune tolerance was not induced in the transplant recipient patient.

In certain embodiments, the present invention provides a method, comprising: (a) obtaining a first blood sample from a transplant recipient patient to detect a baseline frequency of target cells, wherein the first blood sample is obtained pre-tolerization, pre-transplant, and pre-initiation of transient immunotherapy, (b) obtaining a second blood sample from the patient to detect a post-procedure frequency of target cells, wherein the second sample is obtained post-tolerization, post-transplant, and post-initiation of transient immunotherapy, (c) assaying the first and second blood samples to detect levels of target cells before and after tolerization, (d) identifying the transplant recipient patient as having transplantation tolerance/immune acceptance induced by donor antigens infused under cover of transient immunotherapy when the post-procedure frequency is at least 2-fold greater than the baseline frequency, wherein the target cells are T regulatory Type 1 (Tr1) cells having markers CD49b+, LAG-3+, CD4+. In certain embodiments, the donor antigens are apoptotic donor leukocytes (ADLs), donor-specific transfusion (DST) nanoparticles conjugated with donor peptides or encapsulating donor peptides, and/or apoptotic recipient leukocytes conjugated with donor peptides. In certain embodiments, the target cells are T regulatory Type 1 (Tr1) cells having markers CD49b+, LAG-3+, CD4+, have indirect specificity for at least one mismatched donor MHC class I peptide, have a transcriptomic signature indicative of antigen-specific signaling, and have a transcriptomic signature indicative of an activated state.

In certain embodiments, the transplant recipient patient has transplantation tolerance maintained. In certain embodiments, the transplant recipient patient had immune tolerance induced but failed. In certain embodiments, immune tolerance was not induced in the transplant recipient patient.

In certain embodiments, the present invention provides a method of identifying a transplant recipient patient having transplantation tolerance induced by peritransplant infusions (i.e., infusions around the time of transplant; with at least one infusion taking place days prior to the transplant) of apoptotic donor leukocytes under the cover of transient immunotherapy, comprising: (a) assaying a first blood sample from the patient to detect a baseline frequency of target cells, wherein the first blood sample is obtained pre-tolerization, pre-transplant, and pre-initiation of transient immunotherapy, (b) assaying a second blood sample from the patient to detect a post-procedure frequency of target cells, wherein the second sample is obtained post-tolerization, post-transplant, and post-initiation of transient immunotherapy; and (c) identifying the patient as having transplantation tolerance/immune acceptance induced by apoptotic donor leukocytes when the post-procedure frequency is at least 2-fold greater than the baseline frequency, wherein the target cells are T regulatory Type 1 (Tr1) cells, defined as $CD49b^+$, $LAG-3^+$, $CD4^+$ cells. In certain embodiments, the Tr1 cells have indirect specificity for at least one mismatched donor MHC class I peptide (verified using recipient-specific MHC class-II tetramers loaded with said MHC class I peptides), have a transcriptomic signature indicative of antigen-specific signaling, and/or have a transcriptomic signature indicative of an activated state. In certain embodiments, the target cells are T regulatory Type 1 (Tr1) cells having markers $CD49b^+$, $LAG-3^+$, $CD4^+$, have indirect specificity for at least one mismatched donor MHC class I peptide, have a transcriptomic signature indicative of antigen-specific signaling, and have a transcriptomic signature indicative of an activated state. In certain embodiments, the transplant recipient patient having transplantation tolerance induced by donor antigen administered under cover of transient immunotherapy has transplantation tolerance maintained.

As used herein, the term "under the cover of transient immunotherapy" means that the recipient transiently receives immunotherapy agents, such as immunosuppression drugs that target, among other cells, antigen presenting cells and their activation of donor-reactive T cells, any CD40 expressing cell, and T and B cells directly. As used herein "transient" means that the effects of the therapy lasts only for a short time, such as for a few days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days), or for a few weeks (e.g., 1, 2, 3, 4, 5, 6, 7, 8, 9, 10, 11, or 12 weeks), or for a few months (e.g., 1, 2, 3, 4, 5, 6, 7, 8, 9, 10, 11, or 12 months). As used herein, "immunosuppression" means the partial or complete suppression of the immune response, wherein the body's immune system is intentionally stopped from working, or is made less effective, than when the body is not receiving an immunosuppressive drug. In certain embodiments, the immunotherapy also includes the transient administration of anti-inflammatory therapies.

In certain embodiments, the present invention provides a method, comprising: (a) obtaining a first blood sample from a transplant recipient patient to detect a baseline frequency of target cells, wherein the first blood sample is obtained pre-tolerization, pre-transplant, and pre-initiation of transient immunotherapy, (b) obtaining a second blood sample from the patient to detect a post-procedure frequency of target cells, wherein the second sample is obtained post-tolerization, post-transplant, and post-initiation of transient immunotherapy, (c) assaying the first and second blood samples to detect levels of target cells before and after tolerization, (d) identifying the patient as having transplantation tolerance/immune acceptance induced by apoptotic donor leukocytes when the post-procedure frequency is at least 2-fold greater than the baseline frequency, wherein the target cells are T regulatory Type 1 (Tr1) cells, defined as $CD49b^+$, $LAG-3^+$, $CD4^+$ cells. In certain embodiments, the Tr1 cells have indirect specificity for at least one mismatched donor MHC class I peptide, have a transcriptomic signature indicative of antigen-specific signaling, and/or have a transcriptomic signature indicative of an activated state. In certain embodiments, the target cells are T regulatory Type 1 (Tr1) cells having markers $CD49b^+$, $LAG-3^+$, $CD4^+$, have indirect specificity for at least one mismatched donor MHC class I peptide, have a transcriptomic signature indicative of antigen-specific signaling, and have a transcriptomic signature indicative of an activated state.

In certain embodiments, the present invention provides a method of treating a transplant recipient, the method comprising: (a) identifying the transplant recipient patient having transplantation tolerance/immune acceptance induced by apoptotic donor leukocytes (ADLs) infused under cover of transient immunotherapy using the method described above, and (b) treating the transplant recipient patient by ceasing to administer immunosuppressants.

BRIEF DESCRIPTION OF DRAWINGS

FIG. 1C. Transcription profile of Tr1 cells. Left panel: transcriptional levels of XBP1, SUMO2 and SH2D2 are presented as scatter plot in PBL obtained at the time of termination. Right panel: relative expression profile of NDUFS4 and NDUFS5 in PBL obtained at the time of termination in Cohorts B and C recipients are presented as scatter plot.

FIG. 2. Increased frequency of Tr1 cells in tolerant animals. ADL infusions increase the frequency and function of immune cells with regulatory phenotypes. Relative numbers of circulating cells with regulatory phenotypes in Cohort B (n=7, circles) and Cohort C (n=5, square) monkeys. Tr1 cells in PBLs, LMNCs and LNs at time of termination.

FIG. 3. Depletion of Tr1 cells in tolerant animals restores donor-specific proliferation. Depletion of Tr1, Treg and Breg cells in PBLs of Cohort C (n=3) collected at 12 months posttransplant restored donor-specific proliferation of $CD4^+$, $CD8^+$ and $CD20^+$ cells in a CFSE-MLR.

FIG. 4. Silencing of SH2D2a by siRNA in Tr1 cells abolishes suppression of donor-specific proliferation. RNA silencing of SH2D2 in Tr1 cell incapacitate its suppressive capacity. Fold-change in donor-specific proliferation of $CD4^+$, $CD8^+$ and $CD20^+$ cells without Tr1 cells, Tr1 cells+ vehicle and Tr1 cells treated with siRNA targeting SH2D2 transcription molecules compared to donor-treated recipient PBLs only.

FIG. 5. Flow gating strategies for tetramer staining. Increased frequency of $tetramer^+$ donor-specific Tr1 cells in tolerant animals. Percentage of Treg cells (CD25+CD127−) within gated $tetramer^+$ $CD4^+$ lym among Cohort B, C, and D monkeys.

(FIG. 6A) Immunotherapy protocols including treatment products, dosages, routes, and timelines in Cohorts B and C monkeys. sTNFR, soluble Tumor Necrosis Factor Receptor (etanercept); anti-IL-6R, anti-IL-6 Receptor (tocilizumab); IE, islet equivalent. (FIG. 6B) Kaplan-Meir estimates of rejection-free islet allograft survival confirmed by histology show superior sustained allograft survival in the Cohort C (ADLs; n=5; solid line) compared with the Cohort B (no ADLs; n=7; dashed line; P=0.021, Mantel-Cox).

DETAILED DESCRIPTION OF THE INVENTION

Figure 1A:
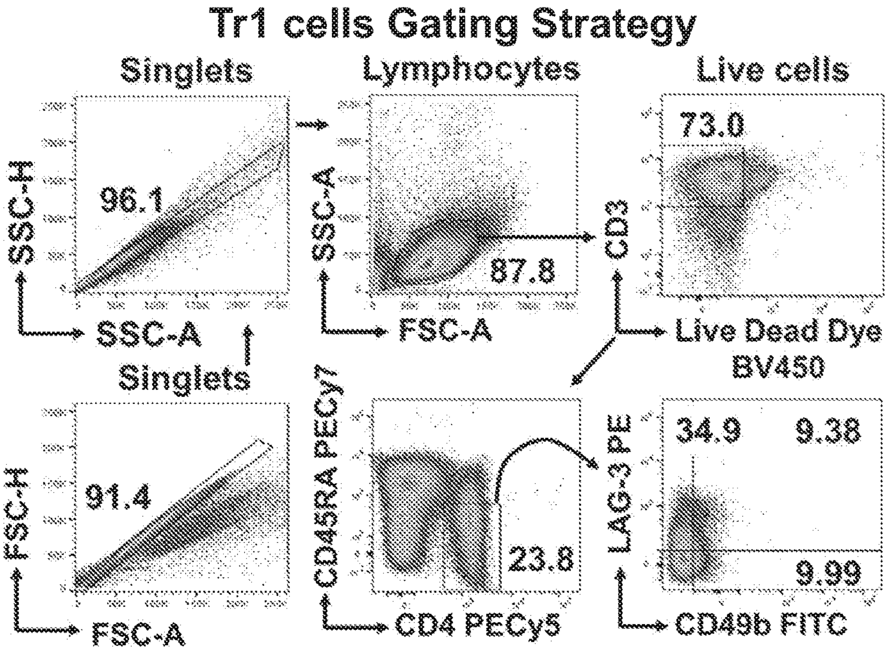
FIG. 1A. Flow gating strategy for Tr1 cells. (a) Tr1 cells ($CD49b^+LAG-3^+$ gated on $CD4^+CD45RA-$ of $CD3^+$ T cells) excluding doublets and dead cells.
Figure 1B:
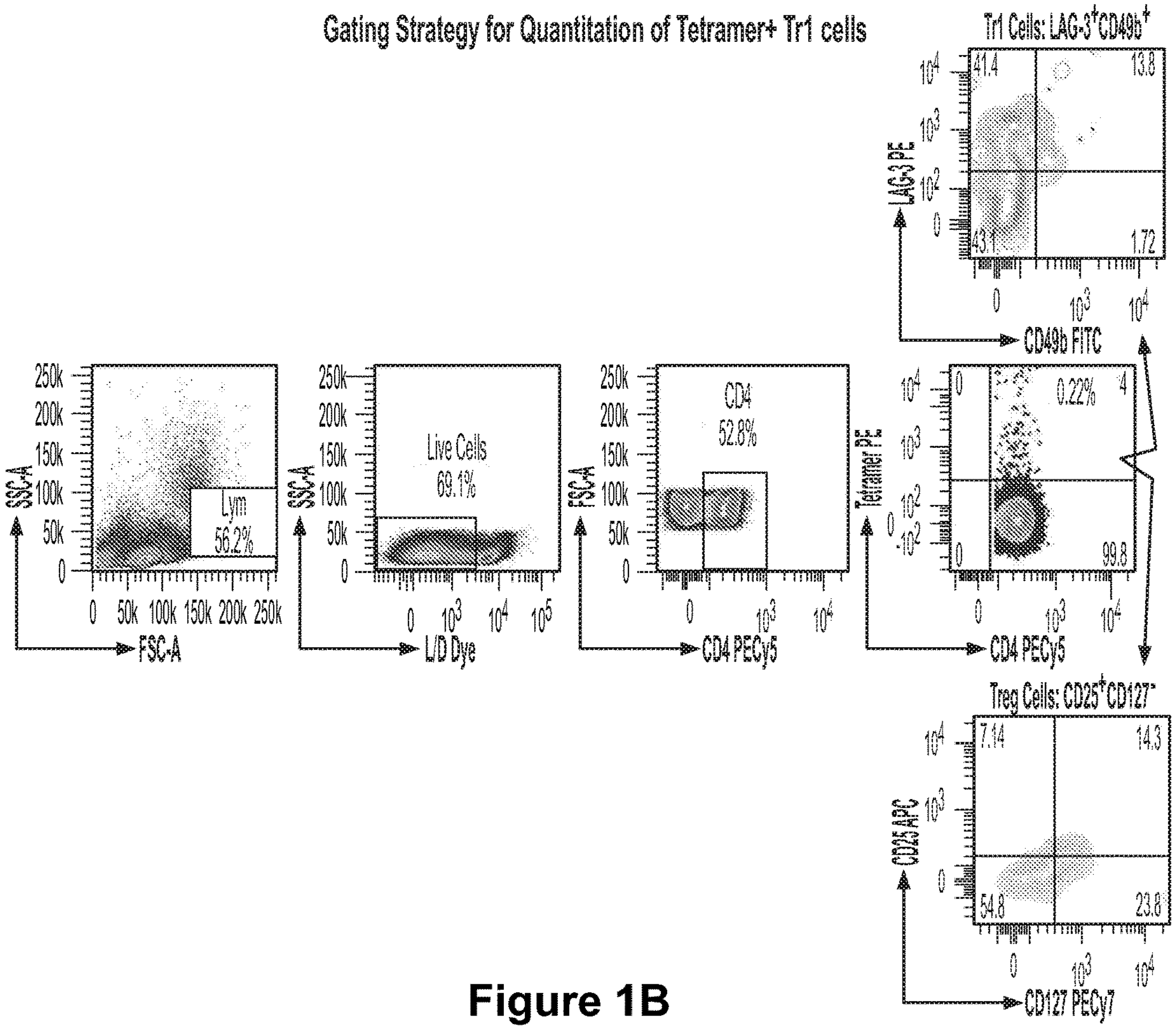
FIG. 1B. Flow gating strategies for tetramer staining. Flow gating strategy showing enumeration of $tetramers^+$ total CD4 T cells, Tr1 and Treg cells.

Negative vaccination with apoptotic donor leukocytes (ADLs) represents a promising, nonchimeric strategy for inducing donor antigen-specific tolerance in transplantation. Leukocytes treated ex vivo with the chemical cross-linker ethylcarbodiimide (ECDI) underwent rapid apoptosis after intravenous infusion. In murine allotransplant models, intravenous infusions of ECDI-treated apoptotic donor splenocytes on days −7 and +1 (relative to transplant on day 0) induced robust and alloantigen-specific tolerance to minor antigen-mismatched skin grafts, to fully major histocompatibility complex (MHC)-mismatched islet allografts, and, when combined with short-term rapamycin, to heart allografts. Most donor ECDI-treated splenocytes were quickly internalized by splenic marginal zone antigen presenting cells (APCs), whose maturation after uptake of apoptotic bodies was arrested, resulting in selective upregulated negative, but not positive, costimulatory molecules.

After encountering recipient APCs, T cells with indirect allospecificity rapidly increased in number, followed by profound clonal contraction; the remaining T cells were sequestered in the spleen, without trafficking to allografts or allograft-draining lymph nodes. Residual donor ECDI treated splenocytes that were not internalized by host phagocytes weakly activated T cells with direct allospecificity, rendering them resistant to subsequent stimulation (anergy). ECDI-treated splenocytes also activated and increased the number of regulatory T (Treg) and myeloid-derived suppressor cells (MDSCs). Thus, in murine allotransplant models, mechanisms of graft protection induced by alloantigen delivery via ECDI-treated splenocytes involved clonal anergy of antidonor CD4+ T cells with direct specificity, clonal depletion of antidonor CD4+ T cells with indirect specificity, and regulation by CD4+ Treg cells and MDSC.

In murine models of autoimmunity and allergy, intravenous delivery of antigens cross-linked with ECDI to the surface of syngeneic leukocytes restored antigen-specific tolerance. Importantly, that strategy prevented both priming of naïve T cells and effectively controlled responses of existing memory/effector CD4+ and CD8+ T cells. A clinical trial involving multiple sclerosis patients affirmed the safety of intravenous delivery of encephalitogenic peptides after ECDI-coupling to autologous leukocytes, also yielding preliminary evidence of efficacy.

In the present study, considerably extending the findings on ECDI-treated donor splenocytes in murine allografts, we demonstrated stable tolerance to islet allografts in rhesus macaques (referred to as monkeys) given 2 ADL infusions under transient immunosuppression. We found that lasting tolerance in our model was associated with depletion of donor-specific T and B cell clones and, most prominently in recipients of 1 MHC class II (MHC-II) allele-matched ADL and allografts, potent and sustained regulation. Several immune cell subsets, including antigen-specific Tr1 cells, participated in immune regulation, suppressing posttransplant expansion of donor reactive T cells and their recruitment to allografts.

Transplantation tolerance induced by ADLs is associated with a sustained increase of regulatory immune cell subsets, including Tr1 cells with distinct specificities and transcriptomic signatures, thereby identifying a biomarker for monitoring the induction, maintenance, and loss of regulatory tolerance induced by ADLs infused intravenously under the cover of transient immunosuppression. Greater than 2-fold increased frequency between baseline and post-procedure blood samples of $CD49b^+$ $LAG\text{-}3^+$ of circulating $CD4^+$ T cells (Tr1 cells) that exhibit indirect specificity for at least 1 mismatched donor MHC class I peptide and transcriptomic signatures indicative of antigen specific signaling (e.g., SH2D2a) and mitochondrial respiration associated with an activated state (e.g., NDUFS4) is indicative of transplantation tolerance.

In certain embodiments, the present invention provides a method of identifying a transplant recipient patient having transplantation tolerance induced by peritransplant infusions of apoptotic donor leukocytes under the cover of transient immunotherapy, comprising: a method of identifying a transplant recipient patient having transplantation tolerance induced by peritransplant infusions of apoptotic donor leukocytes under the cover of transient immunotherapy, comprising: (a) assaying a first blood sample from the patient to detect a baseline frequency of target cells, wherein the first blood sample is obtained pre-tolerization, pre-transplant, and pre-initiation of transient immunotherapy, (b) assaying a second blood sample from the patient to detect a post-procedure frequency of target cells, wherein the second sample is obtained post-tolerization, post-transplant, and post-initiation of transient immunotherapy; and (c) identifying the patient as having transplantation tolerance/immune acceptance induced by apoptotic donor leukocytes when the post-procedure frequency is at least 2-fold greater than the baseline frequency, wherein the target cells are T regulatory Type 1 (Tr1) cells, defined as $CD49b^+$, $LAG\text{-}3^+$, $CD4^+$ cells. In certain embodiments, the Tr1 cells have indirect specificity for at least one mismatched donor MHC class I peptide (verified using recipient-specific MHC class-II tetramers loaded with said MHC class I peptides), have a transcriptomic signature indicative of antigen-specific signaling, and/or have a transcriptomic signature indicative of an activated state.

In certain embodiments, the present invention provides a method, comprising: (a) obtaining a first blood sample from a patient to detect a baseline frequency of target cells, wherein the first blood sample is obtained pre-tolerization, pre-transplant, and pre-initiation of transient immunotherapy, (b) obtaining a second blood sample from the patient to detect a post-procedure frequency of target cells, wherein the second sample is obtained post-tolerization, post-transplant, and post-initiation of transient immunotherapy, (c) assaying the first and second blood samples to detect levels of target cells before and after tolerization, (d) identifying the patient as having transplantation tolerance/immune acceptance induced by apoptotic donor leukocytes when the post-procedure frequency is at least 2-fold greater than the baseline frequency, wherein the target cells are T regulatory Type 1 (Tr1) cells, defined as $CD49b^+$, $LAG\text{-}3^+$, $CD4^+$ cells. In certain embodiments, the Tr1 cells have indirect specificity for at least one mismatched donor MHC class I peptide, have a transcriptomic signature indicative of antigen-specific signaling, and/or have a transcriptomic signature indicative of an activated state.

In certain embodiments, the present invention provides a method of treating a transplant recipient patient, the method comprising: (a) identifying the transplant recipient patient as described herein and (b) treating the transplant recipient patient by ceasing to administer immunosuppressants.

It is important to determine if a transplant recipient patient is acquiring and maintaining immune tolerance to the transplant. In certain embodiments, the transplant that the patient received will be an allotransplant. As used herein, the term "allotransplant" is defined as a transplant of cells, tissues, or organs to a recipient from a genetically non-identical (i.e., distinct) donor of the same species. The transplant may be called an allograft, allogeneic transplant, or homograft. In certain embodiments, the allotransplant is a solid organ allotransplant, such as a kidney, pancreas, liver, intestine, heart, lung, or uterus transplant. In certain embodiments, the allotransplant is a tissue allotransplant, including but not limited to adipose tissue, amniotic tissue, chorionic tissue, connective tissue, dura, facial tissue, gastrointestinal tissue, glandular tissue, hepatic tissue, muscular tissue, neural tissue, ophthalmic tissue, pancreatic tissue, pericardia, skeletal tissue, skin tissue, urogenital tissue, and vascular tissue. In certain embodiments, the allotransplant is a cellular allotransplant, such as an islet, hepatocyte, myoblast, embryonic stem cell-derived differentiated cell transplant (e.g., islet or islet beta cell or hepatocyte transplant), or an induced pluripotent stem cell-derived differentiated cell transplant (e.g., islet or islet beta cell transplant), hematopoietic stem cell transplant, or bone marrow transplant.

As used herein, "immune acceptance," "immune tolerance," "immunological tolerance," or "immunotolerance" is a state of unresponsiveness of the immune system to substances or tissue that have the capacity to elicit an immune response in given organism. The term "transplantation tolerance" is a form of immune tolerance. "Transplantation tolerance" is the long-term allograft survival in the absence of maintenance immunosuppressive therapy. Implicit to this definition is that tolerant recipients of organ transplants are unresponsive to donor antigens but maintain reactivity to other (third-party) antigens. Organ transplant recipients who have been successfully weaned from immunosuppression and have maintained stable graft function for 1 year or more are referred to as functionally or operationally tolerant.

Immunotherapies

In certain circumstances, the transplant recipient patient will have received an immune therapy prior to, concurrently with, or subsequent to transplant, in order to induce transplantation tolerance, where the immune therapy is the administration of apoptotic donor leukocytes (ADLs).

In certain embodiments, the patient received immunotherapy prior to, concurrently with, or subsequent to a transplant. In certain embodiments, apoptotic donor leukocytes can be administered with, or in addition to, one or more immunomodulatory molecules such as antagonistic anti-CD40 mAb antibody, Fc-engineered anti-CD40L antibodies, a peptide interfering with CD40:CD40L co-stimulation, mTOR inhibitor (e.g., sirolimus, everolimus), and transient anti-inflammatory therapy including compstatin (e.g., the compstatin derivative APL-2), cytokine antagonists (e.g., anti-IL-6 receptor mAb (tozilizumab), anti-IL-6 antibody (sarilumab, olokizumab), soluble TNF receptor (etanercept), anti-TNF-alpha antibodies (e.g., infliximab (Remicade), adalimumab (Humira)), al-antitrypsin, nuclear factor-KB inhibitors (e.g., dehydroxymethylepoxyquinomycin (DHMEQ)), ATG (anti-thymocyte globulin) and other polyclonal T cell-depleting antibodies, alemtuzumab (Campath), anti-IL-2R Abs (basiliximab), B-cell targeting strategies (e.g., B cell depleting biologic, for example, a biologic targeting CD20, CD19, or CD22, and/or B cell modulating biologic, for example, a biologic targeting BLyS, BAFF, BAFF/APRIL, CD40, IgG4, ICOS, IL-21, B7RP1), mycophenolate mofetil, mycophenolic acid, down-regulators of down regulating sphingosine-1 phosphate receptors (e.g., FTY720), JAK inhibitors (e.g., tofacitinib), immunoglobulin (e.g., IVIg), CTLA4-Ig (Abatacept/Orencia), belatacept (LEA29Y, Nulojix), tacrolimus (Prograf), cyclosporine A, leflunomide, anti-CXCR3 antibody, anti-ICOS antibody, anti-OX40 antibody, and anti-CD122 antibody, deoxyspergualin, soluble complement receptor 1, cobra venom factor, complement inhibitors (e.g., C1 inhibitor, compstatin), anti C5 antibody (eculizumab/Soliris), methylprednisolone, azathioprine. Non-limiting examples of B-cell targeting biologics include Rituximab and anti-CD20 antibody.

In certain embodiments, the transient immunotherapy comprises at least one immunosuppressant. In certain embodiments, the immunosuppressant is an inhibitor of CD40:CD40L co-stimulation, an mTOR inhibitor, and concomitant anti-inflammatory therapy targeting proinflammatory cytokines. In certain embodiments, the inhibitor of CD40:CD40L co-stimulation is an antagonistic anti-CD40 antibody, an Fc-engineered (disabled, silent) or Fab' anti-CD40L antibody, or a peptide interfering with CD40:CD40L co-stimulation. In certain embodiments, the inhibitor of CD40:CD40L co-stimulation is antagonistic anti-CD40 mAb 2C10R4. In certain embodiments, at least one immunosuppressant is Rapamycin. In certain embodiments, the transient immunotherapy comprises an anti-inflammatory agent. In certain embodiments, the anti-inflammatory agent is anti-IL-6R (tocilizumab) and/or sTNFR (etanercept).

In certain embodiments, to prevent activation of the immune system and induction of anti-donor immunity by the infusion of apoptotic donor leukocytes on days −7 and +1 relative to the transplant on day 0, the recipients were transiently immunosuppressed with drugs that target, among other cells, antigen presenting cells and their activation of donor-reactive T cells, other CD40-expressing cells, or T and B cells directly. Methods of preparing and administering apoptotic donor leukocytes is known in the art. Luo X, Pothoven K L, McCarthy D, DeGutes M, Martin A, Getts D R, Xia G, He J, Zhang X, Kaufman D B, Miller S D, ECDI-fixed allogeneic splenocytes induce donor-specific tolerance for long-term survival of islet transplants via two distinct mechanisms. Proc Natl Acad Sci USA. 2008 Sep. 23; 105(38):14527-32; Miller et al. U.S. Pat. No. 8,734,786. The first dose of each immunosuppressant was given on day −8 or −7 relative to the transplant on day 0. The antagonistic anti-CD40 mAb 2C10R4 was given IV at 50 mg $kg^{-1}$ on days −8, −1, 7, and 14. Rapamycin (Rapamune®) was given PO from day −7 through day 21 posttransplant; the target trough level was 5 to 12 ng mL-t. Concomitant anti-inflammatory therapy consisted of i) αIL-6R (tocilizumab, Actemra®) at 10 mg $kg^{-1}$ IV on days −7, 0, 7, 14, and 21, and ii) sTNFR (etanercept, Enbrel®) at 1 mg $kg^{-1}$ IV on days −7 and 0 and 0.5 mg $kg^{-1}$ SC on days 3, 7, 10, 14, and 21.

In certain embodiments, a first dose of immunosuppressant is administered to the patient seven to fourteen days before transplant (e.g., −1, −2, −3, −4, −5, −6, −7, −8, −9, −10, −11, −12, −13, −14 days). In certain embodiments, a second dose of immunosuppressant is administered to the transplant recipient patient a few days after transplant (e.g., day +1, +2, +3, +4, +5, +6, +7, +8, +9, +10, +11, +12, +13, +14, +15, +16, +17, +18, +19+, or +20). In certain embodiments, multiple doses of immunosuppressant are administered to the transplant recipient (e.g., 2, 3, 4, 5, 6, 7, 8, 9, or 10 doses) in the span of the treatment period of a few days to a few months.

The therapies can be administered through a chosen route of administration. The therapy may be administered intravenously, intraperitoneally or intramuscularly by infusion or injection.

Target Cells

In certain embodiments of the present invention, a first (baseline) biological sample, such as a blood sample, is obtained from the patient prior to immune therapy and transplantation ("pre-tolerization"). In certain embodiments, on day −7 the patient receives an infusion of apoptotic donor cells, on day 0 the transplant recipient patient receives the transplant, and on day +1 the transplant recipient patient receives a second infusion of apoptotic donor cells. A second biological sample is obtained after transplantation ("post-transplant"), and a third sample is obtained after the second infusion of apoptotic donor cells. In certain embodiments, a fourth biological sample is obtained after the first infusion of cells and the transplant. From these samples, very specific target cells are isolated, namely, cells that are identified as T regulatory Type 1 (Tr1) cells, defined as $CD49b^+$, $LAG\text{-}3^+$, $CD4^+$ cells. In certain embodiments, the Tr1 cells have indirect specificity for at least one mismatched donor MHC class I peptide, have a transcriptomic signature indicative of antigen-specific signaling, and/or have a transcriptomic signature indicative of an activated state. Tolerogenic Tr1 cells are a subset of $CD4^+$ T cells that are thought to be an important mediator of tolerance/immune acceptance induced by the peritransplant infusions of apoptotic donor leukocytes.

Major histocompatibility complex (MHC) class II tetramer staining enables the characterization, quantification and sorting of defined, antigen-specific $CD4^+$ T cells. MHC tetramers are an essential tool for characterizing antigen-specific $CD4^+$ T cells. Protocols for the ex vivo tetramer staining of comparatively rare antigen-specific $CD4^+$ T cells have provided a crucial tool for T-helper-cell analysis in basic and clinical immunology. (Uchtenhagen, H. et al. Efficient ex vivo analysis of CD4+ T-cell responses using combinatorial HLA class II tetramer staining. Nat. Commun. 7, 12614 (2016); Day, C. L. et al. Ex vivo analysis of human memory CD4 T cells specific for hepatitis C virus using MHC class II tetramers. J. Clin. Invest. 112, 831-842 (2003); Kwok, W. W. et al. Direct ex vivo analysis of allergen-specific CD4 T cells. J. Allergy Clin. Immunol. 125, 1407-1409.e1401 (2010); Moon, J. J. et al. Naive CD4+ T cell frequency varies for different epitopes and predicts repertoire diversity and response magnitude. Immunity 27, 203-213 (2007)). Accordingly, MHC class II tetramer staining has become an invaluable approach in immunology, enabling direct interrogation of the naturally developing T-cell repertoire, assessment of changes in T-cell responses caused by perturbations such as vaccination and disease, and providing a means of confirming the translational relevance of observations in model systems.

It is known in the art to identify $CD4^+$ T-cells that are $CD49b^+$ and $LAG\text{-}3^+$ using flow cytometry and gating. These $CD49b^+LAG\text{-}3^+$ $CD4^+$ T-cells are referred to as Tr1 cells. In certain embodiments, the frequency of Tr1 cells in the samples is determined by multiparametric flow cytometry. A subset of Tr1 cells with indirect specificity are identified using MHC class II tetramers loaded with mismatched donor MHC class I peptides. In certain embodiments, this powerful tetramer technology tracks these rare and donor peptide-specific cell subsets. In certain embodiments, the frequency of Tr1 cells is determined by CyTOF mass cytometry.

Next, the specific target cells, i.e., $CD4^+$ T-cells that are $CD49b^+$ and $LAG\text{-}3^+$ were analyzed to determine if they have indirect specificity for at least one mismatched donor MHC class I peptide. This determination of the presence of at least one mismatched donor MHC class I peptide is generated using multiparametric flow cytometry. In certain embodiments, the mismatched donor MHC class I peptide is APVALRNLRGYYNQS, a 14-mer peptide in the variable region of the MHC class I molecule (28-114 aa). A t-BLAST analysis was performed of the Mamu DRB sequence with the human genome at the NCBI website to determine the human homolog. HLA DRB1*13 (Acc. No. CDP32905.1) was 92% identical, with 96% positives and 0% gaps to the Mamu DRB03a with an e value of 6e-178 and HLA DRB1*14 (Acc. No. ABN54683.1) was 93% identical, with 94% positives and 0% gaps to the Mamu DRB04 with an e value of 2e-175.

Peptides from Mamu MHC class I and class II sequence with high binding affinity for HLA DRB1*13 or HLA DRB1*14 were identified (Table 1) using the Immune Epitope Database Analysis resource.

TABLE 1

MHC class I Peptides that bind to MHC Class II molecule.

| Tetramer | Source Antigen | Sequence | Position |
|---|---|---|---|
| HLA-DRB1*14:01 | Mamu-A4 | APVALRNLRGYYNQS | 98 |
| HLA-DRB1*14:01 | Mamu-A8 | SLRYFYTAVSRPGRG | 28 |
| HLA-DRB1*14:01 | Mamu-A8 | TRIYKAATQNYREGL | 88 |
| HLA-DRB1*14:01 | Mamu-A1 | SMKYFYTSMSRPGRG | 28 |
| HLA-DRB1*14:01 | Mamu-A1 | WEPFSQSTIPMVGII | 298 |
| HLA-DRB1*14:01 | Mamu-A2/49 | SMRYFYTSMSRPGRW | 28 |
| HLA-DRB1*03:01 | Mamu-A4 | TQFVRFDSDAASQRM | 55 |
| HLA-DRB1*03:01 | Mamu-A8 | TQFVRFDSDAESPRE | 55 |
| HLA-DRB1*03:01 | Mamu-A2 | APVNLRNLRGYYNQS | 98 |
| HLA-DRB1*14:01 | Mamu-A2 | APVNLRNLRGYYNQS | 98 |

TABLE 1-continued

| MHC class I Peptides that bind to MHC Class II molecule. | | | |
|---|---|---|---|
| Tetramer | Source Antigen | Sequence | Position |
| HLA-DRB1*03:01 | Mamu-DR3a | YVRFDSDVGEHRAVS | 66 |
| HLA-DRB1*14:01 | Mamu-DR4 | GAGLFIYFRNQKGPS | 243 |
| HLA-DRB1*14:01 | Mamu-DR1a | GAGLFIYFRNQKGHT | 243 |

The specific target cells were also analyzed to determine their transcriptomic signature indicative of antigen-specific signaling. As used herein the "transcriptomic signature" of a cell is the expression level of RNAs in a cell population. Briefly, RNA from the sorted target cells is analyzed by using quantitative real-time PCR using a set of primers and probes selected and defined by previous unbiased RNAseq analyses of cells from transplant recipients with documented and stable tolerance. In certain embodiments of the present invention, quantitative real-time PCR was done on RNA obtained from flow-sorted Tr1 cells. In certain embodiments, the transcriptomic signature indicative of antigen-specific signaling is SH2 Domain Containing 2A (SH2D2a).

TABLE 2

| Feature ID | EDGE test: cohort B vs cohort C, tagwise dispersions - Fold change | EDGE test: cohort B vs cohort C, tagwise dispersions - P value |
|---|---|---|
| Differentially Expressed Transcripts in Tr1 cells. Immune Activation | | |
| ABI2 | 191.78 | 1.89E-03 |
| ANAPC11 | 98.37 | 3.75E-03 |
| BATF | 76.83 | 8.13E-03 |
| CCR5 | 20.49 | 4.87E-03 |
| CD300E | 92.87 | 4.38E-03 |
| CYB5R3 | 17.44 | 2.21E-03 |
| DSC3 | 63.55 | 2.04E-03 |
| HMGB1 | 20.04 | 7.53E-03 |
| IFNLR1 | 43.08 | 8.41E-03 |
| ISG15 | 61.67 | 8.45E-03 |
| MAPK7 | 31.08 | 5.49E-03 |
| MBL2 | 1024.92 | 2.22E-03 |
| NANOG | 60.09 | 7.55E-03 |
| NCK1 | 30.04 | 5.07E-03 |
| POLR3K | 72.95 | 9.27E-03 |
| PROS1 | 187.13 | 4.81E-03 |
| SH2D2A | 21.11 | 3.54E-03 |
| SLC27A2 | 93.21 | 5.46E-03 |
| TOM1 | 31.54 | 1.41E-03 |
| TRIM68 | 33.12 | 4.01E-03 |
| TUBB2B | 53.27 | 2.74E-03 |
| Signal Transduction | | |
| ABI2 | 191.78 | 1.89E-03 |
| ACKR1 | 1136.81 | 3.96E-03 |
| ARHGEF38 | 1008.09 | 2.19E-03 |
| CCR5 | 20.49 | 4.87E-03 |
| CNKSR2 | 356.54 | 7.04E-03 |
| CTTN | 87.42 | 2.73E-03 |
| DISP2 | 183.45 | 2.61E-03 |
| DLG3 | 450.87 | 2.29E-04 |
| GAB1 | 72.27 | 5.04E-03 |
| GFRA1 | 107.2 | 7.10E-03 |
| HIST1H4L | 488.58 | 5.07E-03 |
| ITGB3 | 259.36 | 5.00E-03 |
| LRP5 | 183.98 | 5.35E-03 |
| MAPK7 | 31.08 | 5.49E-03 |
| MCF2L | 391.04 | 4.75E-04 |

TABLE 2-continued

| Feature ID | EDGE test: cohort B vs cohort C, tagwise dispersions - Fold change | EDGE test: cohort B vs cohort C, tagwise dispersions - P value |
|---|---|---|
| Differentially Expressed Transcripts in Tr1 cells. Immune Activation | | |
| MIS12 | 90.09 | 6.24E-03 |
| NCBP2 | 17.43 | 6.87E-03 |
| NCK1 | 30.04 | 5.07E-03 |
| P2RY2 | 235.71 | 4.15E-03 |
| PMEPA1 | 95.68 | 5.75E-03 |
| PRKAG1 | 17.32 | 7.96E-03 |
| RGS16 | 39.93 | 3.99E-03 |
| RGS18 | 215.98 | 3.55E-03 |
| RNF2 | 218.7 | 3.32E-03 |
| SH2D2A | 21.11 | 3.54E-03 |
| SKA2 | 25.53 | 5.64E-03 |
| TUBB2B | 53.27 | 2.74E-03 |
| Metabolism | | |
| ACBD4 | 56.83 | 9.42E-03 |
| ACOT7 | 72.59 | 9.50E-03 |
| ADI1 | 88.84 | 3.70E-03 |
| ADO | 35.39 | 1.81E-03 |
| COQ2 | 88.53 | 6.22E-03 |
| CYB5R3 | 17.44 | 2.21E-03 |
| CYP2C8 | 356.35 | 9.30E-03 |
| GDPD5 | 99.21 | 4.19E-03 |
| GK | 82.51 | 9.38E-03 |
| ISCA1 | 47.9 | 3.13E-03 |
| LIPT1 | 72.99 | 9.35E-03 |
| MCEE | 23.58 | 4.40E-03 |
| MMADHC | 35.8 | 6.00E-03 |
| MTRR | 13.47 | 8.76E-03 |
| NDUFB1 | 29.03 | 8.62E-03 |
| NDUFS4 | 27.47 | 8.19E-03 |
| PFKP | 16.23 | 4.22E-03 |
| PHKA1 | 42.34 | 2.30E-03 |
| PRKAG1 | 17.32 | 7.96E-03 |
| RPL7 | 1100.39 | 1.29E-04 |
| RPSA | 28.9 | 5.69E-03 |
| SGMS2 | 498.32 | 7.37E-03 |
| SLC27A2 | 93.21 | 5.46E-03 |
| SULT4A1 | 512.47 | 5.82E-03 |
| UGCG | 25.35 | 5.83E-03 |
| UGT2A1 | 356.35 | 9.30E-03 |
| ZDHHC21 | 90.5 | 6.61E-03 |
| Gene Expression | | |
| E2F8 | 173.1 | 4.67E-03 |
| HIST1H4L | 488.58 | 5.07E-03 |
| MOBP | 694.57 | 8.32E-03 |
| MYBL2 | 20.93 | 7.45E-03 |
| NCBP2 | 17.43 | 6.87E-03 |
| PLAGL1 | 20.18 | 8.92E-03 |
| POLR3K | 72.95 | 9.27E-03 |
| PRKAG1 | 17.32 | 7.96E-03 |
| RNF2 | 218.7 | 3.32E-03 |
| SNAPC5 | 82.01 | 7.02E-03 |
| TTF1 | 15.69 | 6.13E-03 |
| ZNF181 | 20 | 8.94E-03 |
| ZNF253 | 71.19 | 9.18E-03 |
| ZNF398 | 19.22 | 8.55E-03 |
| ZNF426 | 69.53 | 3.97E-03 |
| ZNF441 | 35.1 | 2.29E-03 |
| ZNF684 | 70.74 | 9.26E-03 |
| ZNF688 | 134.9 | 3.00E-03 |
| ZNF75D | 26.53 | 7.43E-03 |

In certain embodiments, the transcriptomic signature is indicative of an activated state. In certain embodiments, the transcriptomic signature indicative of an activated state is mitochondrial respiration-associated transcript NADH:Ubiquinone Oxidoreductase Subunit S4 (NDUFS4).

Transplants

In certain embodiments, the transplant is an allotransplant. In certain embodiments, the allotransplant is a solid organ allotransplant. In certain embodiments, the allotransplant is a solid organ allotransplant, such as a kidney, pancreas, liver, intestine, heart, lung, or uterus transplant. In certain embodiments, the solid organ allotransplant is a kidney transplant. In certain embodiments, the allotransplant is a tissue allotransplant, including but not limited to adipose tissue, amniotic tissue, chorionic tissue, connective tissue, dura, facial tissue, gastrointestinal tissue, glandular tissue, hepatic tissue, muscular tissue, neural tissue, ophthalmic tissue, pancreatic tissue, pericardia, skeletal tissue, skin tissue, urogenital tissue, and vascular tissue. In certain embodiments, the allotransplant is a cellular allotransplant, such as an islet, hepatocyte, myoblast, embryonic stem cell-derived differentiated cell transplant (e.g., islet or islet beta cell or hepatocyte transplant), or an induced pluripotent stem cell-derived differentiated cell transplant (e.g., islet or islet beta cell transplant), hematopoietic stem cell transplant, or bone marrow transplant.

In certain embodiments, the transplant is a living donor transplant. In certain embodiments, the allotransplant is a cellular transplant.

Assay Methods

In certain embodiments, the present invention involves the steps of (a) assaying a first blood sample from a patient to detect a baseline frequency of target cells, wherein the first blood sample is obtained pre-tolerization, pre-transplant, and pre-initiation of transient immunotherapy, (b) assaying a second blood sample from the patient to detect a post-procedure frequency of target cells, wherein the second sample is obtained post-tolerization, post-transplant, and post-initiation of transient immunotherapy; and (c) identifying the patient as having transplantation tolerance/immune acceptance induced by apoptotic donor leukocytes when the post-procedure frequency is at least 2-fold greater than the baseline frequency, wherein the target cells are T regulatory Type 1 (Tr1) cells, defined as $CD49b^+$, $LAG\text{-}3^+$, $CD4^+$ cells. In certain embodiments, the Tr1 cells have indirect specificity for at least one mismatched donor MHC class I peptide, have a transcriptomic signature indicative of antigen-specific signaling, and/or have a transcriptomic signature indicative of an activated state.

In certain embodiments, the frequency of target cells in the first (baseline) sample is compared to the frequency of target cells in the second (post-procedure) sample and subsequent samples. In certain embodiments, the determination of at least a 2-fold increase in the frequency indicates tolerance/immune acceptance induced by the peritransplant infusion of apoptotic donor leukocytes. In certain embodiments, the determination of at least a 3-fold increase in the frequency indicates tolerance/immune acceptance induced by the peritransplant infusion of apoptotic donor leukocytes. In certain embodiments, the frequency between the first and second sample is at least 2× increase, at least a 3× increase, at least a 4× increase, at least a 5× increase, at least a 10× increase, at least a 20× increase, at least a 30× increase, at least a 50× increase, at least a 60× increase, at least a 70×, at least a 80× increase, at least a 90× increase, at least a 100×, or higher-fold increase.

In certain embodiments, the frequency of the target cells is determined by multiparametric flow cytometry. In certain embodiments, the frequency of the target cells is determined by CyTOF mass cytometry.

In certain embodiments, the transplant recipient patient has received two peritransplant, intravenous infusions of apoptotic donor leukocytes.

In certain embodiments, peripheral blood mononuclear cells from the transplant recipient patient is stained with a defined cocktail of fluorescence-conjugated antibodies and markers (anti-CD4, anti-CD49b, anti-LAG3, MHC class-II tetramer loaded with mismatched donor MHC class I peptides) to facilitate sorting of labeled cells using microfluidic technology, and the labeled cells are characterized using subsequent quantitation of the tolerance-associated transcripts using quantitative real time PCR.

The percentage of such defined $CD4^+$ $CD49b^+$ $LAG3^+$ T cells (Tr1 cells) with indirect specificity for mismatched donor peptides and expressing transcripts indicating antigen-specific TCR signaling (SH2D2a) and indicating a metabolically active state (NDUFS4)) is exceedingly low at baseline. A more than 2- to 3-fold increase in the percentage of that circulating T cell subset cannot be explained other than the presence of an antigen-specific tolerant state.

The invention will now be illustrated by the following non-limiting Examples.

Example 1

Transplantation tolerance has been pursued for decades as a clinically relevant goal. In the present study, it was demonstrated that a regimen of 2 peritransplant ADL infusions under short-term immunotherapy safely induced long-term (≥1 year) tolerance to islet allografts in 5 of 5 nonsensitized, 1 MHC-II DRB allele-matched monkeys. These findings, obtained in a stringent preclinical allotransplant NHP model, are unique and point to the first clinically applicable path toward nonchimeric transplantation tolerance in humans.

Previous NHP studies reported tolerance to renal, but not heart or islet allografts, when donor bone marrow was given under nonmyeloablative conditioning, including CD154 blockade. Of the 8 monkeys so treated in one of those studies, 6 maintained renal allograft function in the absence of maintenance immunosuppression for 1 year; moreover, 3 of them maintained long term function without developing chronic rejection. Using nonchimeric strategies in another study, tolerance of renal allografts was attained, but only inconsistently, in 3 of 5 monkeys that received donor-specific transfusions combined with anti-CD40L for 8 weeks and rapamycin for 90 days. A similar NHP strategy, as well as other previously investigated strategies, prolonged islet allograft survival after discontinuation of maintenance immunosuppression or on rapamycin monotherapy, but unlike our study, none of these protocols induced lasting tolerance. In contrast to other cell-based tolerance strategies currently being investigated, our regimen did not require the adoptive transfer of regulatory cells; instead, we found that peritransplant ADL infusions under short-term immunosuppression established potent and sustained immunoregulation in-vivo involving several regulatory cell types. With respect to safety, our regimen, unlike the mixed chimerism strategy, effectively induced stable tolerance without requiring irradiation, indiscriminate generalized T cell deletion, simultaneous hematopoietic stem cell transplantation, or a course of either calcineurin inhibitors or anti-CD8 depleting antibodies for control of early posttransplant direct pathway activation. Finally, unlike other antigen specific strategies involving soluble peptide and altered peptide ligand therapy, our ECDI fixed leukocyte infusions were not associated with the risk of anaphylaxis or with any other safety concerns in our preclinical study or in a clinical trial in multiple sclerosis.

Several distinct immune mechanisms were associated with our 1 DRB-matched ADL infusions under transient immunosuppression and tolerance to islet allografts. The regimen depleted alloreactive effector T and B cells early after 2 peritransplant ADL infusions, as evidenced in Cohort A by our observation of tracking Ki67+ proliferating cells, alloreactive proliferation in MLR, proliferating TCRβ clones, and CD4+ T cells with indirect specificity for mismatched MHC class I allopeptides in our tetramer studies. Previous murine studies showed that uptake of apoptotic bodies by APCs following ADL infusions substantially increased PD-L1/2 expression while downregulating positive costimulation12. APCs exhibiting such patterns rapidly (but transiently) activated T cells that produce IFN-γ and IL-10 but not IL-2, IL-6, and TNF-α, a cytokine microenvironment known to promote apoptotic depletion of antigen-specific T cells. Rapamycin, part of our concomitant immunotherapy, potentiates the activation-induced cell death triggered by donor antigen under CD40:CD40L blockade.

In the present study, suppression was noted in Cohort C (but not in Cohorts B and D) of the posttransplant expansion of circulating CD4+ and CD8+ TEM cells, their recruitment to the graft, and the proliferation of donor-reactive CD4+ and CD8+ T cells in-vitro. These findings suggest that our ADL infusions and 1 DRB-matching did play important roles in tolerance induction and maintenance. The restored T cell proliferation to donor that we observed in-vitro after depletion of regulatory subsets suggests that donor-specific T cell clones were neither deleted nor anergized, but rather that regulation controlled their posttransplant expansion and effector function.

Further supporting that interpretation, we showed that the addition of ADL infusions to short term immunosuppression in Cohort C established a regulatory network characterized by significant and sustained increases in circulating MDSCs and Tr1, Treg, NS, Breg, and B10 cells. At termination, Tr1 cells were also significantly more prevalent within livers bearing allografts and in lymph nodes of Cohort C (versus Cohort B) recipients. The detailed mechanisms underlying the formation of that regulatory network remain to be defined. Nonetheless, it is possible that our 1 DRB-matched ADL infusions provided copious amounts of shared MHC-II peptides for presentation by MHC-II molecules on host spleen marginal zone APCs and on host liver sinusoidal endothelial cells. It is known that after trogocytosis to activated T cells, such peptide MHC-II complexes can deliver potent activation signals to thymus-derived Treg (tTreg) cells, which have a TCR repertoire skewed toward self-recognition. Treg cells are known to promote the generation of IL-10-producing Tr1 cells46, but it remains to be determined whether the expansion of Tr1 cells in our study was due to the influence of activated tTregs and resulted from de-novo formation and/or conversion of donor reactive T effector cells. In autoimmunity models, Tl-like cells, generated by nanoparticles coated with autoimmune disease-relevant peptides bound to self MHC-II, are known to contribute to regulatory network formation by driving the differentiation of cognate B cells into disease-suppressing regulatory B cells. Consistent with the idea that matched MHC-II peptides facilitated regulatory networks in our study, the frequency of circulating Treg, Tr1, and Breg cells in Cohort C recipients of 1 DRB-matched ADLs was significantly higher than the frequency in fully mismatched Cohort D recipients.

Among regulatory subsets, it was found that Tr1 cells exhibited the most potent suppression of donor-specific proliferation of T and B cells, which was mediated in part through IL-10. In contrast, third-party responses were not affected by sorted Tr1 cells, indicating their antigen specificity. In Cohort C (but not in Cohorts B and D), our tetramer studies revealed sustained posttransplant increases in circulating Treg and Tr1 cells with indirect specificity for mismatched donor MHC-J peptides. That finding corroborated their antigen specificity and was consistent with previous studies of murine and human allograft recipients showing regulation induced by mismatched MHC-I peptide presentation by shared self MHC-II molecules after 1 MHC-II allele matched blood transfusions. ADLs increased regulatory subsets in fully mismatched murine allograft recipients6; the effect of MHC-II matching in these models remains to be studied. In Cohort C recipients, Tr1 cells exhibited unique immune cell signaling, including significantly increased levels of SH2D2. T cell-specific adapter protein (TSAd), the gene product of Sh2D2a, regulates TCR signaling through its interaction with Lck51; however, its absence promotes systemic autoimmunity. In Cohort C, Tr1 cell transcriptomic profiles also demonstrated increased mitochondrial respiratory activity and energy utilization in Tr1 cells, revealing their activated state.

Figure 7:
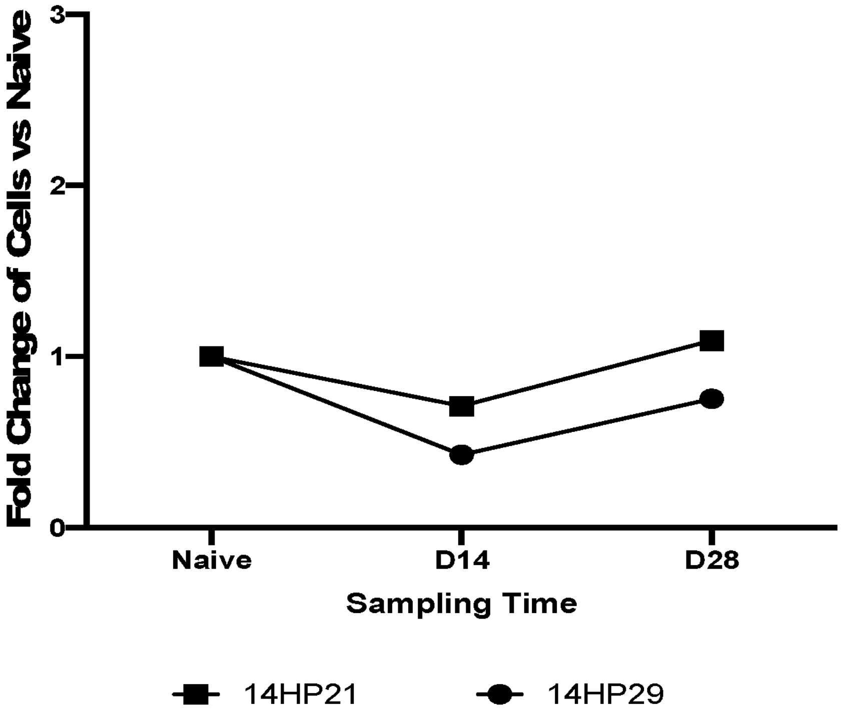
FIG. 7. Absence of tolerance biomarker correlates with early loss of transplanted graft function in recipients sensitized to donor antigens at baseline pre-transplant. The frequency of Tr1 cells in peripheral circulation (pre-ADL+TIS and post transplantation) were analyzed by flow cytometry. ADL infusions and TIS in recipients sensitized to donor antigens pretransplant resulted in a significant reduction—instead of increase—in the frequency of Tr1 cells on day 14 post-transplant. By day 28 post-transplant, the frequency of circulating Tr1 cells reached the levels observed in the naïve status of the same recipients in whom pretransplant sera demonstrated evidence of sensitization to donor antigen at baseline. The monitoring of Tr1 cells in these recipients, even without monitoring specifically for Tr1 cells with indirect specificity for mismatched donor MHC class I peptides and a highly defined transcriptomic profile, strongly suggested that ADL infusions and TIS had failed to induce immune tolerance to donor alloantigens in these recipients.
Figure 8:
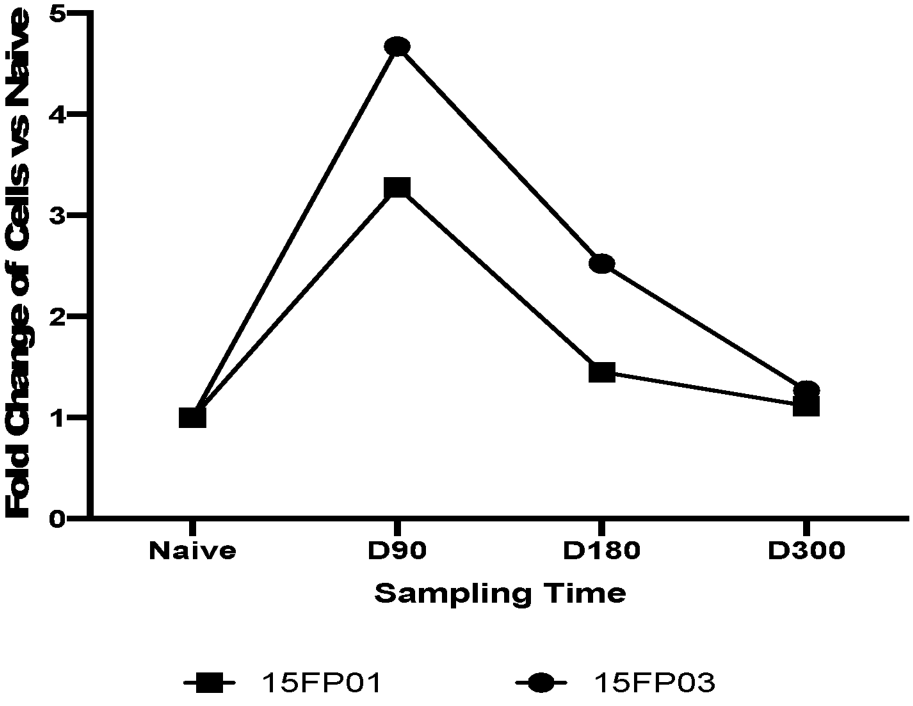
FIG. 8. Loss of tolerance biomarker precedes the loss of transplanted graft function. The frequency of Tr1 cells in peripheral circulation (pre-ADL+TIS and post transplantation) were analyzed by flow cytometry. ADL infusions and TIS resulted in a significant increase in the frequency of Tr1 cells early post-transplant. The circulating frequency of Tr1 cells started declining at day 180 post-transplant and reached the levels observed in naïve status on day 300, indicating the loss of tolerance biomarker precedes the loss of graft function.

In Cohort B (no ADL infusions), 2 of 7 recipients maintained immunosuppression-free allograft survival for 1 year posttransplant, and all 7 avoided acute rejection, confirming that favorable allograft survival can be achieved when early direct pathway activation is suppressed with potent induction in MHC-II matched recipients. However, this regimen failed to control indirect pathway activation, as evidenced by de-novo DSA development in most Cohort B recipients. The tolerogenic efficacy of 1 DRB-matched ADL infusions under transient immunosuppression was limited in sensitized Cohort E recipients, particularly in those with preformed DSAs, in whom memory T cells, including those not secreting IFN-γ, are mandatory for DSA responses, and in whom APCs, activated by uptake of DSA-opsonized ADLs, likely primed instead of tolerized donor-reactive T cells. FIGS. 7 and 8 present data in islet transplant recipients that were part of a Cohort that was sensitized to donor antigens at baseline (FIG. 7) and in recipient monkeys that were fully mismatched with the their donors at MHC class I and class II (including also the DRB alleles) (FIG. 8).

Methods

Study Animals

The cohorts included purpose-bred monkey (*Macaca mulatta*) donors and recipients of Indian origin obtained from the National Institute of Health and Infectious Diseases colony at AlphaGenesis, Inc, Yemassee, SC. The exploratory group included 3 males age 7.3±0.1 years and weighed 12.5±1.5 kg. The control cohort included 8 males age 4.3±2.1 years and weighed 6.2±1.6 kg. Experimental cohort included 7 males and 1 female age 4.1±1.7 years and weighed 5.2±1.2 kg. The donor cohort included 19 males age 6.7±3.3 years and weighed 11.7±3.6 kg. Animals were free of herpes virus-1 (B virus), simian immunodeficiency virus (SIV), type D simian retrovirus (SRV), and simian T-lymphotropic virus (STLV-1). Eligibility additionally included ABO compatibility, and study-defined MHC matching (MHC-I-disparate and 1 MHC-II DRB allele-matched donor-recipient pairs). All animals underwent high-resolution MHC-I and -II genotyping by 454 pyrosequencing (Genetics Services Unit at the Wisconsin National Primate Research Center) 60. They had free access to water and were fed biscuits (Harlan Primate Diet 2055C, Harlan Teklad, Madison, WI) based on body weight (BW). Their diet was enriched daily with fresh fruits, vegetables, grains, beans, nuts, and a multivitamin preparation. Semi-annual veterinary physical examinations were performed on all animals. Animals were socially housed and participated in an environmental enrichment program designed to encourage sensory engagement, enhance foraging behavior, novelty seeking, promote mental stimulation, increase exploration, play and activity levels, and strengthen social behaviors, together providing opportunities for animals to increase time budget spent on species typical behaviors. Monkeys were trained to cooperate in medical procedures including hand feeding and drinking, shifting into transport cages, and presentation for exam, drug administration, metabolic testing, and blood collection and instrumented with indwelling central and intraportal vascular access. Diabetes was induced with STZ (100 mg/kg IV) and was confirmed by basal C-peptide <0.3 ng/mL and negative C-peptide responses to intravenous glucose challenge 61. Monitoring of recipient monkeys included daily clinical assessments by study staff, regular evaluations by veterinary staff, and weekly hematology and chemistry laboratory studies. The care and treatment of all animals in this study were conducted with the approval of the University of Minnesota Institutional Animal Care and Use Committee and in compliance with the recommendations in the *Guide for the Care and Use of Laboratory Animals* (Institute of Laboratory Animal Resources, National Research Council, U.S. Department of Health and Human Services).

Flow Cytometric Analysis of Immune Cell Phenotypes

Multicolor flow cytometric analyses were performed on cryopreserved peripheral blood mononuclear cells (PBLs), tissue-infiltrating mononuclear cells from liver (LMNCs) and lymph node (LNs) samples of Cohort B-E monkeys. $1\times10^6$ cells were stained with viability dye (Aqua; Life Technologies) to discriminate viable cells from cell debris. The cells were stained for 25 min at RT with antibodies, fluorescence-minus-one (FMO) and/or isotype controls, followed by fixation (eBiosciences) and wash. To assess regulatory T cells and proliferating T and B cells and intracellular cytokines, PBL were stained with antibodies recognizing extracellular epitopes (CD3, CD4, CD8, CD25, and CD127), followed by fixation/permeabilization with FoxP3 Fixation/Permeabilization kit (eBioscience) and staining with anti-FoxP3, Ki67, IFN-γ, IL-10 and TGF-β antibodies. A minimum of 200,000 events were acquired on 3-laser BD Canto II (BD Bioscience) with FACSDIVA 6.1.3. Relative percentages of each of these subpopulations were determined using FlowJo 10.1 software (TreeStar).

Gating Strategy

First, cells were gated on FSC-H versus FSC-A, and then on SSC-H versus SSC-A to discriminate doublets. FIGS. 1A-1C, FIG. 2. Lymphocytes were then gated based on well-characterized SSC-A and FSC-A characteristics. Dead cells were excluded based on viability dye. The following phenotypic characteristics were used to define immune cell populations: T cells: $CD3^+$ lymphocytes; $CD4^+$ T cells: $CD4^+/CD3^+/CD8$; $CD8^+$ T cells: $CD8^+/CD3^+/CD4^-$; CD4 or CD8 TEM cells were determined as $CD2^{hi}/CD28^-$ within CD4 or CD8 T cells. Expression of PD-1, Tbet, CD40 and Ki67 were determined on both $CD4^+$, $CD8^+$ T cells and $CD20^+$ B cells. Chemokines receptor (CXCR-5) expression was examined on CD4 T cells to enumerate Tfh cells: $CXCR5^+$ $CD4^+$ T cells. Regulatory T cells were defined as Tr1 cells: $CD49b^+LAG\text{-}3^+$ of gated $CD4vCD45RA^-$ lymphocytes, Treg cells: CD127-$FoxP3^+$ of gated $CD4^+CD25^+$ lymphocytes, Natural Suppressor (NS) cells: $CD8^+$ $CD122^+$ of gated CD8 lymphocytes and for Breg cells: regulatory B cells ($CD24^{hi}CD38^{hi}$), B10 cells: ($CD24^{hi}$ $CD27^+$) within $CD3^-$ $CD19^+/CD20^+$ lymphocytes based on expression of CD24, CD27 and CD38 antigens. Gated $Lin^-$ ($CD3^-CD20^-$) $HLA\text{-}DR^-$ $CD14^+$ cells were analyzed, to enumerate Myeloid Derived Suppressor Cells (MDSC): $CD11b^{hi}CD33^{hi}$ of $CD14^+Lin–HLA\text{-}DR^-$ cells.

Donor-Specific T and B Cell Responses

Mixed lymphocyte reactions (MLRs) were performed on cryo-banked PBL samples from islet donors and transplant recipients. Responder PBLs (300,000 cells) samples from recipient monkeys, were labeled with 2.5 μM CFSE (Invitrogen, Cat #C34554) and were co-cultured with irradiated (3000 cGy) VPD-450-labeled (BD, Cat #562158) stimulator PBLs (300,000 cells) from islet donors (donor) and unrelated MHC-mismatched donors (third-party). In another set of experiments, CFSE-labelled PBL from naïve responder monkeys, were co-cultured (300,000 cells) with ECDI-fixed PBLs (ADLs) from islet donors. Apoptotic donor leukocytes (ADLs) were prepared. On day 6 of MLR, CFSE dilution was measured on $CD4^+$, $CD8^+$, and $CD20^+$ cells, and presented in percentage of CFSE low cells as proliferative cells.

Assessment of multifunctional cytokine profile of donor stimulated Tr1 cells. T cells from the peripheral blood from Cohort B (n=3), Cohort C (n=3), and Cohort E (n=2) monkeys were collected at time of termination. Briefly, responder recipients PBLs ($1\times10^6$ cells) were cultured in the presence of donor PBLs (VPD-450 labeled) at 1:1 ratio for 48 hrs. These donor-primed cells were briefly activated with low-dose of PMA/Ionomycin for 4 hours in the presence of Brefeldin-A (10 ug/ml). Cells were surface-stained for CD4, CD49b, and LAG-3 followed by permealization fixation and intracellular staining for IL-10 and TGF-β. Gating strategy to identify Tr1 cells was performed as described above.

ELISPOT. For IFN-7 ELISPOT assays, longitudinally collected PBLs from Cohort B and Cohort C monkeys were thawed, washed, and pre-incubated in a 12-well culture plate at 37° C., 5% $CO_2$ with donor PBLs in a final volume of 1 ml CRPMI medium. After 48 hours, cells were harvested, washed twice with PBS, and resuspended in 200 μl of culture medium. Cells were transferred to 2 ELISPOT wells coated with anti-IFN-γ antibody, and incubated in a final volume of 100 μl per well for 5 hours at 37° C. Subsequently, the ELISPOT assay (U-Cytech Biosciences) was executed according to the manufacturer's protocol. Spot analysis was performed with an Immune Spot ELISPOT reader (CTL).

Sensitization Screening (Donor Specific Antibodies, DSAs). Sera from recipient RM were collected at different time points and presence of DSAs was detected by flow cytometry. In brief, preserved donor PBLs were thawed and after washing with complete RPMI, resuspended in $4\times10^6$ cells/ml in FACS buffer (PBS containing 2% FBS). 50 μl of prepared cell suspension was seeded in each well of U-shape 96 well plate along with 50 μl of complement deactivated (56° C. for 45 minutes) recipient's serum followed by 30 minutes incubation at room temperature, 3 times PBS wash. Finally re-suspended in 100 μl of FACS buffer with FITC-anti-IgG, PE-anti-CD20, PE Cy7-anti-CD3 and LIVE/DEAD™ Fixable Aqua dye followed by incubation for 20 minutes at RT. After incubation, cells were washed twice, fixed with paraformaldehyde, and analyzed by BD FACS Canto II Flow Cytometer. Detection of anti-IgG levels on $CD3^+$ gated cells represent the amount of DSAs in each recipient's serum.

Suppression Assays Examining Immune Regulation

All designated regulatory subpopulations were sorted from Cohort C monkeys. PBLs obtained from freshly collected blood were labeled with CD4, CD49b, and LAG-3 for Tr1 cell ($LAG\text{-}3^+$ $CD49b^+$ of $CD4^+$) sorting, CD19, CD24, CD38 for Breg cell ($CD24^+$ $CD38^+$ of $CD19^+$) sorting, and CD4, CD25, CD127 for Treg cell (CD25 $hi^+$ $CD127^-$ of CD4$^{+}$) sorting in sterile PBS followed by wash. The BD FACSAria II system was set up for a sort using an 85-μm nozzle (45 psi with a frequency of 47 kHz). All the sortings were performed at 8,000 to 10,000 events per second. Sorted cells were collected in 12×75-mm round bottom tubes with CRPMI. Post sort analyses were performed for purity assessment.

In depletion assays, Treg, Breg, and Tr1 cells were depleted from PBLs of Cohort C monkeys, collected at 12 months post-transplant. FIG. 3. Identical numbers of CFSE-labeled total PBLs (nondepleted) or Treg-depleted (non CD4$^{+}$ lym plus CD127$^{-}$CD25$^{hi}$ CD4$^{+}$ lym), Breg-depleted (non CD19$^{+}$ lym plus CD24$^{-}$CD38$^{-}$ CD19$^{+}$ lym), and Tr1-depleted (non CD4$^{+}$ lym plus CD49b$^{-}$ LAG3$^{-}$ CD4$^{+}$ lym) PBLs were cultured with equal numbers of irradiated, VPD450-labeled donor PBLs in a 1-way CFSE Flow-MLRs for 6 days. For all CFSE-MLR proliferation assays, a 1:1 ratio of responder and stimulator cells was maintained. During flow analysis of proliferating cells (CFSE$^{-}$), the entire donor population were excluded based on VPD450$^{+}$ positivity.

To ascertain the suppressive capacity of sorted cells, naïve recipient PBLs, collected at baseline before vaccination and transplantation, were challenged with irradiated VPD450-labeled donor PBL cells (1:1 ratio) in 1-way CFSE Flow-MLR for 3-4 days followed by re-challenge with irradiated, donor PBLs in the presence or absence of various types and ratios (1:50) of immune cells with regulatory phenotypes (Tr1, Treg, and Breg cells). These cells were sorted from tolerant recipients between 9 and 12 months post-transplant. For all suppression assays examining Tr1 cells, a 1:50 ratio of Tr1 vs total PBLs was used in the presence of donor and third-party donor. Transwell experiments were set up to study whether Tr1-mediated suppression is contact dependent. In this set of experiments, CFSE-labeled Tr1-depleted PBLs were seeded (300,000 cells) in the bottom of the plate with irradiated, VPD450-labeled donor cells (1:1 ratio) in the presence or absence or Tr1 cells separated by the transmembrane (4 μm pore size, Corning, Ref #3391), either in the presence (10 μg/ml) or absence of anti-human IL-10 neutralizing Ab, known to cross-react with IL-10 of monkeys, and matched isotype.

siRNA Mediated SH2D2 Inhibition in Tr1 Cells

Flow sorted Tr1$^{+}$ cells (CD49b$^{+}$LAG-3$^{+}$CD4$^{+}$) and Tr1− lym cells (pool of CD4$^{-}$ Lym$^{+}$ CD49b$^{-}$ LAG-3$^{-}$ of CD4$^{+}$) were sorted from PBLs of Cohort C monkeys collected at 12 months post-transplant. CFSE-labelled Tr1− lym cells (300,000) were cultured with or without VPD-450 labelled irradiated donor cells (300,000) for 6 days MLR. Initially, sorted Tr1 cells are rested for first 3 days in CRPMI and later they were treated with 100 μM Accell Human SH2D2A siRNA (Dharmacon Accell, Cat #E-017851-00-0005) by combining Accell siRNA stock solution and Accell delivery media (GE Healthcare, Cat #B-005000-500) directly to sorted Tr1$^{+}$ cells. Tr1$^{+}$ cells treated with SH2D2A siRNA or Accell delivery media alone were added back to MLR for last 3 days. To measure the impact of siRNA mediated SH2D2 inhibition on Tr1-mediated suppression of donor-specific T and B cells, on day 6 total culture cell were harvested and stained for assessment of T and B cell proliferation. FIG. 4.

Tetramers Preparation and Staining

To enable tracking of CD4$^{+}$ T cells, Tr1 cells, and Treg cells with indirect allopeptide specificity in these monkeys with MHC class II tetramers, the high degree of similarity observed in the peptide binding motifs of MHC class II molecules in rhesus monkeys, cynomolgus monkeys, and humans was exploited. S t-BLAST analysis was performed of the Mamu DRB sequence with the human genome at the NCBI website to determine the human homolog. HLA DRB1*13 (Acc. No. CDP32905.1) was 92% identical, with 96% positives and 0% gaps to the Mamu DRB03a with an e value of 6e-178 and HLA DRB1*14 (Acc. No. ABN54683.1) was 93% identical, with 94% positives and 0% gaps to the Mamu DRB04 with an e value of 2e-175. Peptides from Mamu MHC class I and class II sequence with high binding affinity for HLA DRB1*13 or HLA DRB1*14 were identified using the Immune Epitope Database Analysis resource. Synthetic peptides (Genscript USA Inc) were loaded onto the HLADRB1*13 or HLA DRB1*14 tetramers. PBL were incubated with 0.5 or 1 μg/ml HLA class II tetramer PE along with the antibodies for specific cell surface markers for 20 min. Stained cells were washed with cold PBS/1% FCS, fixed in 1% PBS/formaldehyde, acquired on BD Canto II and data analysis was performed using FlowJo version 10.2 (Tree Star, Ashland, OR). FIG. 5.

TCR Sequencing for Tracking Donor-Reactive T Cells

An RNA-based, high-throughput sequencing of the TCR 3 chain CDR3 region was employed to compare the entire repertoire of T cell clones at intervals before and after ADL infusions in Cohort A monkeys. This approach has the advantage over genomic methods that require designing and optimizing multiplex primer sets that span the entire V gene segment; these remain poorly defined in monkeys. Total RNA was extracted from frozen PBLs using RNeasy Plus Universal (Qiagen) and first strand cDNA was created from the poly A tailed fraction of total RNA. Briefly, custom designed oligo dT primer and a template switching primer were used in a reverse transcriptase reaction to synthesize cDNA which was used as template for targeted PCR enrichment of the TCR VDJ region using primers specific to the *M. mulatta* TCR constant region and the template switch sequence. Enriched VDJ amplicons from each sample were uniquely dual-indexed by PCR for multiplexing compatibility during sequencing. All PCR amplifications were performed with KAPA HiFi HotStart DNA Polymerase ReadyMix kit (Roche). Indexed amplicon libraries were pooled equimolarly and cleaned with SPRI beads (Ampure XP, Beckman Coulter). The final pool was sequenced on a MiSeq (Illumina) 300 bp paired end run (v3 kit). Preparation and sequencing of TCR NGS libraries was performed at the University of Minnesota Genomics Center. Raw, QC-ed short reads were cleaned via trimmomatic68 using set parameters (ILLUMINACLIP:all_illumina_adapters.fa:2:30:10 LEADING:3 TRAILING:3 SLIDINGWINDOW:4:15 MINLEN:70). The preprocessed reads were directly input into MiXCR69 for TCR profiling with default setting (https://mixcr.readthedocs.io/en/latest/rnaseq.html). Known TRB clone-types in rhesus monkeys was used as reference. The resulted TRB clone-types were further filtered using customized threshold with a clone fraction of ≥0.5%. Frequency of clonal expansion was calculated by dividing the frequency of the clone at individual time points over the average frequency of all the identified mapped TCR clones. Most of the donor-specific TCR clones at the baseline were very low or undetectable hence we had used peak proliferation as baseline and analyzed the fate of those expanding T cell clones.

RNASeq for Examining Gene Expression in Sorted Tr1 Cells

RNA samples were sequenced using the Illumina Hiseq 2500 platform 50 bp paired end reads. Raw sequence that passed CASAV 1.8P/F filter were assessed by fastqc (http://www.bioinformatics.babraham.ac.uk/projects/fastqc). Read mapping was performed via Hisat2 (v2.0.2) using the UCSC human genome (hg38) as reference. Cuffdiff 2.2.1 was used to quantify the expression level of each known gene in units of FPKM (fragment mapped per kilobase of exons per million mapped reads). Differentially expressed genes were identified using the edgeR (negative binomial) feature in CLCGWB (Qiagen, Valencia, CA) using raw read counts. DEG is presented on a color scale. The expressed transcripts were annotated using the nonhuman primate or Human Genome database. The results were ranked by the absolute value of fold change, and DEG between Cohort B and Cohort C were identified. The generated list was filtered based on a minimum 1.5× Absolute Fold Change and raw p values <0.01. These DEGs were imported into Ingenuity Pathway Analysis Software (Qiagen, Valencia, CA) for pathway identification. FIG. 1C.

ADL Processing, Release Testing, and Infusion

On day −7 relative to islet transplantation, splenocytes were isolated from donor monkey spleens, RBC lysed, and remaining cells enriched for B cells with nylon wool columns (Polysciences, Inc.). The cells (80%) were agitated on ice for 1 hour with ECDI (30 mg/ml per $3.2\times10^8$ cells, AppliChem) in DPBS, washed, cleaned of necrotic cells and microaggregates and assessed for viability/necrosis by AO/PI fluorescent microscopy. ECDI-fixed splenocytes were loaded into cold syringes (n=9) or IV bags (n=2) for IV infusion at a target dose of $0.25\times10^9$ cells per kilogram recipient body weight with a maximum concentration of 20×106 cells/mL and remained on ice until recipient administration. Induction of apoptosis was monitored in vitro by incubating ECDI-fixed cells at 37° C. for 4-6 hours, labelling with Annexin V/PI (Invitrogen), and analyzed on fluorescent microscopy.

To meet the target dose of ECDI-fixed ADLs for day +1 infusion, blood drawn from donor monkeys on days −15 and −7 relative to islet transplant and the remaining 20% of splenic cells were enriched for B cells via magnetic sorting using non-human primate CD20 beads (Miltenyi Biotech) and expanded ex-vivo in a GREX100M flask (Wilson Wolf) until day +1 in the presence of rhIL-10 (10 ng/ml), rIL-4 (10 ng/ml), rhBAFF (30 ng/ml), rhTLR9a (10 ng/ml), and either rhCD40L-MEGA or both rhCD40L multimeric (500 ng/ml), and rhAPRIL (50 ng/ml). Expanded cells were stimulated with rhIL-21 (5 ng/ml), 24 hours prior to harvest. Recipients were pretreated prior to infusion with a combination of diphenhydramine 12.5 mg, acetaminophen 160 mg, and ondansetron 4 mg PO.

Transient Immunosuppression

Immunosuppression was administered to all recipient monkeys in Cohorts A-E. To cover all ADL infusions in Cohort A, C, D, and E monkeys, the first dose of each drug was given to all recipients in Cohorts A-E on day −8 or −7 relative to islet transplant on day 0. The antagonistic anti-CD40 mAb 2C10R4, provided by the NIH Nonhuman Primate Reagent Resource, was given IV at 50 mg/kg on days −8, −1, 7, and 14. Rapamycin (Rapamune®) was given PO from day −7 through day 21 posttransplant; the target trough level was 5 to 12 ng/ml. Concomitant anti-inflammatory therapy consisted of i) αIL-6R (tocilizumab, Actemra®) at 10 mg/kg IV on days −7, 0, 7, 14, and 21, and ii) sTNFR (etanercept, Enbrel®) at 1 mg/kg IV on days −7 and 0 and 0.5 mg/kg/SC on days 3, 7, 10, 14, and 21. Exploratory cohort RM were terminated at day +7, accordingly the last dose of immunosuppression was given in these RM on day +7.

Pancreas Procurement, Islet Processing and Release Testing, Islet Transplantation, and Assessment of Islet Graft Function Donor monkeys in Cohorts C-E underwent total pancreatectomy, and islets were isolated, purified, cultured for 7 days to minimize direct pathway stimulatory capacity, and subjected to quality control. On day 0, a target number of ≥5,000 IE/kg by DNA64 with endotoxin contents of ≤1.0 EU/kg recipient BW were transplanted non-surgically using the indwelling intraportal vascular access port into STZ-diabetic RM. Protective exogenous insulin was stopped at day 21 posttransplant in animals with full graft function. Metabolic monitoring included daily am/pm blood glucose, weekly C-peptide, monthly HbA1c, mixed meal testing, and bi-monthly IVGTTs with determination of acute C-peptide response to glucose and glucose disappearance rate (Kg).

Histopathology of Islet Grafts

Liver specimens were obtained from 10 different anatomical areas in each recipient, fixed in 10% formalin, and processed for routine histology. Sections from each of the 10 blocks were stained with hematoxylin & eosin (H&E) or immunostained for insulin to score transplanted islets. Rejection-free islet allograft survival was confirmed by demonstrating at necropsy on graft histopathology a considerable number of intact A-type and mildly infiltrated B-type islets with no or very few C- to F-type islets (moderately to markedly infiltrated islets and islets partially or completely replaced by infiltrates or fibrosis).

ADLs Induce Abortive Expansion of Donor-Specific T and B Cell Clones

Monitoring cellular immunity early after ADL infusions under short-term immunosuppression in 3 nontransplanted, nondiabetic, 1 DRB-matched Cohort A monkeys revealed several findings. The frequency of circulating MDSCs increased significantly, beginning 1 day after the first ADL infusion (day −6) and remained elevated throughout the end of follow-up on day +7. The frequency of $Ki67^+CD4^+$ T cells increased 2.6-fold on day −5, followed by a 90% decline 3 days later and a near-total absence beginning 3 days after the second ADL infusion. The frequency of $Ki67^+CD8^+$ T cells increased 19-fold after the first ADL infusion, followed by a sharp decline beginning 4 days after the first ADL infusion and a near-total absence shortly after the second ADL infusion. After both ADL infusions, $CD20^+$ B cells showed similar kinetics and magnitude of expansion and contraction. The frequency of interferon-gamma (IFN-γ)-secreting $CD4^+$ T cells dropped significantly, the frequency of interleukin (IL)-10-secreting $CD4^+$ T cells remained unchanged. The donor-specific proliferation of $CD4^+$, $CD8^+$ and $CD20^+$ cells dropped significantly, whereas proliferation in response to third-party donors remained unchanged in carboxyfluorescein diacetate succinimidyl ester-mixed lymphocyte reaction (CFSE-MLR) assays.

To track the fate of $CD4^+$ T cells with indirect specificity for the mismatched donor HC-I Mamu A00427-41 peptide, we loaded it on the HLA DRB1*13 (the human homolog of Mamu-DR03) tetramer in 3 Cohort A monkeys. Those cells increased 5.6-fold on day −5, then declined 3.6-fold on day 0. Then, 2 days after the second ADL infusion, the frequency of tetramer-positive $CD4^+$ T cells increased 1.24-fold, but significantly contracted on day 7 versus naïve monkeys.

The clonotype analysis of the VDJ region in these monkeys demonstrated that the frequency of about 30 T cell clones was altered after ADL infusions. Alterations in several T cell clones with different Vβ chains (4-Vβ5, 3 each of Vβ4, Vβ7, Vβ9, Vβ11, Vβ12, and Vβ28) indicated that ADL infusions targeted multiple alloreactive clones; consistent with the notion that alloreactivity is polyclonal. Individual T cell clone analysis demonstrated abortive expansion and subsequent 5- to 8-fold contraction of multiple clones. Thus, several lines of evidence indicated that ADL infusions caused expansion, followed by contraction of donor-specific T and B cells.

ADLs Promote Stable Islet Allograft Tolerance in 1 DRB-Matched RM

Figure 6A:
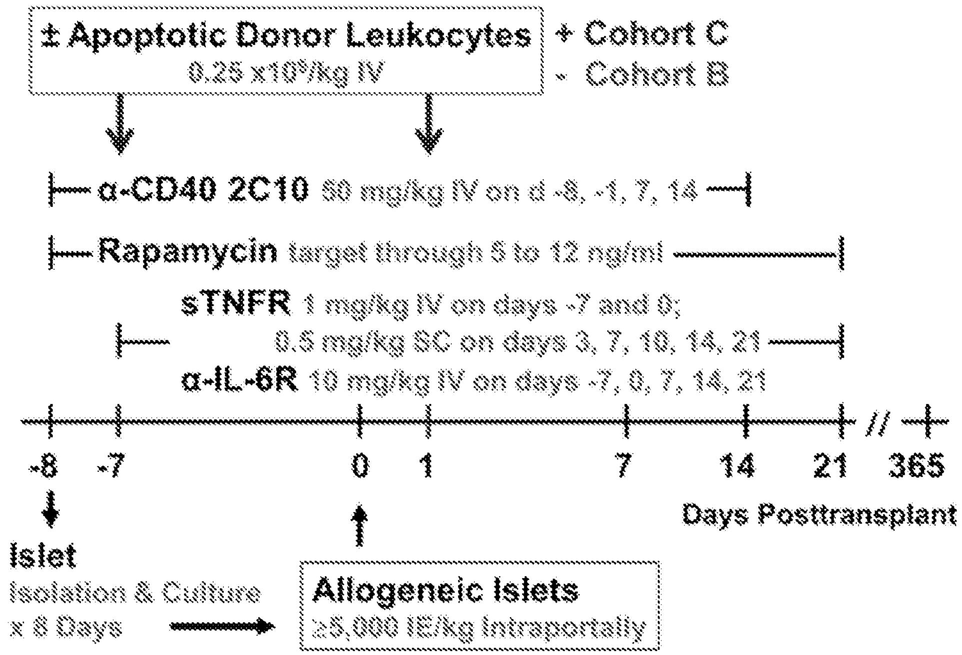
FIGS. 6A-6B. ADL infusions added to transient immunosuppression facilitate stable tolerance of islet allografts in monkeys.
Figure 6B:
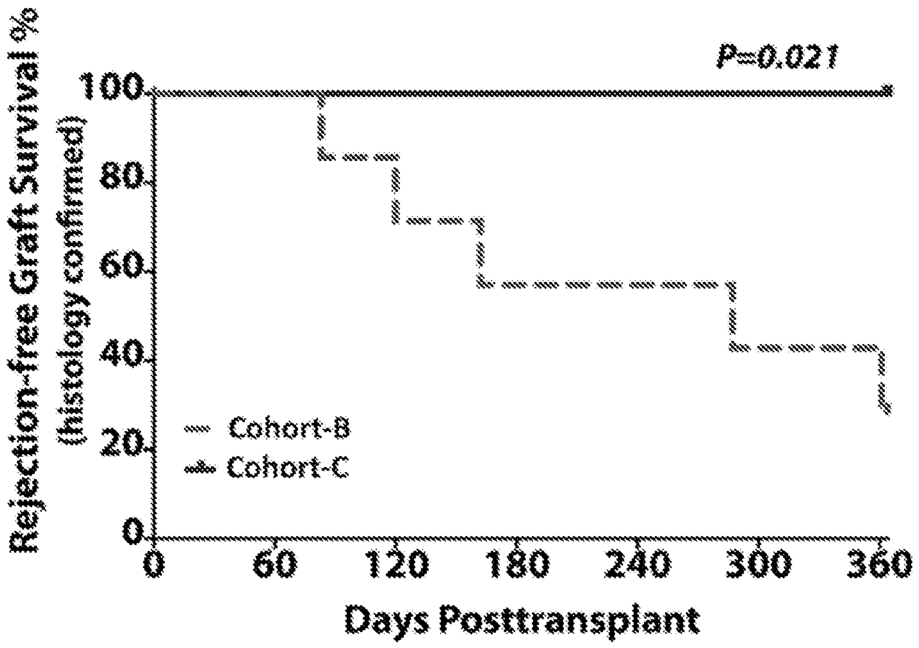

In 2 of 7 streptozotocin (STZ)-diabetic 1 DRB-matched Cohort B monkeys on short-term immunosuppression, intraportal transplants of 8-day cultured islet allografts were accepted for ≥365 days (FIGS. 6*a* and 6*b*). In 5 of 5 Cohort C monkeys, ADL infusions added to short-term immunosuppression was associated with significantly improved survival (P=0.021); all 5 exhibited operational tolerance of islet allografts for ≥365 days posttransplant (FIGS. 6*a*,6*b*). Cohort C monkey #13EP5 became normoglycemic immediately posttransplant and remained so, even after discontinuation of immunosuppression and exogenous insulin on day 21 posttransplant; that recipient's HbA1C level became and remained normal posttransplant. The continued weight gain posttransplant, observed also in other Cohort C monkeys, is consistent with the overall safety of the treatment regimen. Pretransplant serum C-peptide levels and responses to glucose stimulation were negative in all 5 recipients. In monkey #13EP5, the strongly positive posttransplant fasting and random serum C-peptide levels and their increase after stimulation throughout the 1-year follow-up confirmed stable islet allograft function. That recipient showed stable posttransplant blood glucose disappearance rates (Kg) after intravenous challenge with glucose that were comparable with the pre-STZ rate; the C-peptide levels derived from matching tests showed substantial increases of >1 ng/ml throughout the posttransplant course. Histopathologic analysis of that recipient's liver at necropsy revealed numerous intact islets, with no or minimal periislet infiltration. The transplanted, intrahepatic islets showed strongly positive staining for insulin; the absence of insulin-positive islet beta cells in the native pancreas at necropsy indicated that posttransplant normoglycemia reflected graft function and was not due to remission after STZ-induced diabetes. Cohort C monkey #15CP1 was not sacrificed at 1 year posttransplant; islet allograft function continued in that recipient for >2 years after discontinuation of immunosuppression. At necropsy of monkey #15CP1, histopathology confirmed rejection-free islet allograft survival and absence of insulin-positive beta cells in the native pancreas. By comparison, Cohort B monkey #15CP3 became normoglycemic posttransplant but deterioration of graft function was evident starting 4 months posttransplant. Necropsy 1 month later confirmed rejection, evidenced by a small number of insulin-positive islet beta cells heavily infiltrated by mononuclear cells. Together, these results demonstrated the long-term functional and histologic survival of 1 DRB-matched islet allografts in ADL-treated RM, even after discontinuation of immunosuppression, indicating robust tolerance in a stringent, translational model.

ADLs Suppress Effector Cell Expansion and Donor-Specific Antibody (DSA) Elicitation Effector cell and antibody responses were compared in Cohort B and C recipients. The circulating frequency of $CD3^+$, $CD4^+$, and $CD8^+$ T cells and $CD20^+$ B cells at 3, 6, and 12 months posttransplant was not affected by ADL infusions in Cohort C. However, in contrast to Cohort B monkeys not given ADLs, peritransplant ADL infusions in Cohort C were associated with prolonged suppression of expansion of circulating, liver mononuclear cell (LMNCs), mesenteric lymph node (LNs), and anti-donor $CD4^+$ and $CD8^+$ T effector memory (TEM) cells. Throughout the 12-month posttransplant follow-up, ADL infusions were associated with a low frequency of circulating T follicular helper (Tfh) cells in Cohort C compared with Cohort B monkeys. As with PD-$1^+CD4^+$ T cells, the proportion of PD-$1^+CD8^+$ T cells was higher posttransplant in Cohort C versus Cohort B, suggesting T cell exhaust phenotype induction and elimination by ADLs. Our analyses also showed sustained suppression of $Tbet^+$ $CD4^+$ and $CD40^+CD4^+$ T cells in the circulation of Cohort C monkeys, without affecting $CD4^+$ T cell proliferation to third-party donors. The circulating frequency of $Tbet^+CD8^+$, $CD40^+CD8^+$, and $CD107^+CD8^+$ T cells was lower in Cohort C than in Cohort B monkeys at 3 months posttransplant, without compromised proliferation of $CD8^+$ T cells to third-party. The enzyme-linked immunosorbent spot (ELISPOT) analysis revealed no significant differences between Cohorts B and C in the frequency of IFN-γ-secreting T cells with direct and indirect specificities in response to irradiated donor peripheral blood lymphocytes (PBLs) at 1 month and at sacrifice, as well as no significant differences as compared with baseline. The frequency of circulating $CD20^+$ B cells was similar in Cohorts B and C, but the proportion of $Tbet^+$ B cells in the circulation at 3 and 12 months posttransplant and of $CD19^+$ B cells within LMNCs at sacrifice were significantly lower in Cohort C compared with Cohort B monkeys. Only Cohort B, and not Cohort C, recipients developed high DSA levels (expressed by mean fluorescence intensity (mfi)). We did not measure DSAs frequently enough to determine if DSAs were present before clinical rejection. In each of the DSA-positive recipients, rejection was confirmed by histopathologic analysis. Collectively, peritransplant ADL infusions impeded the posttransplant activation and expansion of effector T and B cells, as well as their recruitment to allografts in 1 DRB-matched monkeys on short-term immunosuppression.

ADLs Expand Antigen-Specific Regulatory Networks

Next, we compared frequency of lymphoid and myeloid cells with regulatory phenotypes in Cohort B and C monkeys. We found a significantly higher frequency of T cells in the circulation at 3, 6, and 12 months posttransplant, and of LMNCs and LNs at sacrifice, in ADL-treated Cohort C than in nontreated Cohort B monkeys. In addition, we also found a significantly higher percentage of circulating natural suppressor (NS) and Treg cells throughout the posttransplant follow-up period in ADL-treated Cohort C than in non-treated Cohort B monkeys. Regulatory B (Breg) cells, B10 cells, and MDSCs were also significantly more abundant in the circulation during the posttransplant follow-up period and, except for MDSCs, in the liver and LNs at sacrifice in Cohort C than in Cohort B monkeys. In Cohort C PBLs (as compared with unmodified recipient PBLs) at 9 and 12 months posttransplant, depletion of Treg, Breg, and Tr1 cells was associated with increased $CD4^+$ T (4.9-, 2.1-, and 8.1-fold), $CD8^+$ T (5.3, 4.3-, and 11.1-fold), and CD20+ B (3.1-, 3.0-, and 5.0-fold) cell proliferation to donor. Adding back Tr1 cells sorted from tolerant Cohort C recipients at 12 months posttransplant to PBL collected from recipients at baseline during re-challenge significantly suppressed donor-specific proliferation of $CD4^+$, $CD8^+$, and $CD20^+$ cells, but had no discernible effect on T and B cell proliferation in response to third-party donors. Separation of Tr1 cells in transwell experiments did not block suppression of donor-specific responses, indicating that Tr1 cells suppressed immune responses through soluble factors. Addition of neutralizing IL-10, but not of control isotype antibody, in one-way CFSEMLR assays significantly abrogated suppression of donor-specific responses.

Analysis of differentially expressed genes (DEG) in flow-sorted Tr1 cells from Cohort B and C monkeys identified 258 genes. Grouping the DEG revealed that immune cell-signaling and mitochondrial respiration were 2 major biological pathways activated in sorted Tr1 cells in Cohort C, but Cohort B RM. Our heat map analysis of z-score of DEG demonstrated marked upregulation of immune signaling intermediates in Tr1 cells only in Cohort C. The top 3 regulators of immune cell signaling, i.e., the relative transcripts of SH2D2, XBP1 and SUMO2 were significantly upregulated in Tr1 cells in Cohort C, as compared with Cohort B, indicating that Cohort C Tr1 cells were in an activated state. Our heat map z-score analysis of DEG that mapped to mitochondrial respiration showed that Cohort C Tr1 cells clustered at 1 end, demonstrating that the cells were metabolically highly active. Members of the NDUSF family that regulate mitochondrial respiration, NDUFS4 and NDUFS5, were significantly upregulated in Cohort C Tr1 cells. Treatment of Tr1 cells sorted from a tolerant Cohort C monkeys, at 12 months posttransplant, with small interfering RNA (siRNA) targeting SH2D2 transcription molecules reduced the capacity of Tr1 cells to suppress proliferation of $CD4^+$ (59%), $CD8^+$ (53%), and $CD20^+$ (80.5%) cells in response to donor. Thus, ADLs expanded regulatory networks, involving antigen-specific Tr1 cells that exhibited unique immune cell signaling and metabolic profiles.

The tolerogenic efficacy of ADLs appears blunted in fully mismatched RM ADL infusions in fully mismatched Cohort D monkeys were associated with prolonged allograft function in 2 of 3 recipients. But in the third recipient, the graft was rejected between 120 and 150 days posttransplant; in that recipient, expansion of TEM cells was not suppressed in this recipient. After ADL infusions, the expansion at 6 months posttransplant of Treg (1.4-fold) and Tr1 (0.98-fold) cells in Cohort D was less profound than in Cohort C monkeys (2.3- and 2.1-fold, P=0.04); moreover, in the Cohort D recipient whose graft was rejected, proliferation of donor-specific T cells was not suppressed. The frequency of 3 categories of Tr1 cells—IL-10-, tumor growth factor beta (TGF-β)- and dual IL-10-plus TGF-β-producing—significantly increased in Cohort C, but not Cohort D, as compared with Cohort B. Tr1 cells isolated at the time of sacrifice from 2 Cohort D recipients with long-term allograft function reduced donor reactive proliferation of T and B cells by >45%, as compared with >75% for Cohort C Tr1 cells when added to CFSE-MLRs at the same ratios. Depletion of Tr1 cells from PBLs obtained at sacrifice increased donor-specific proliferation of both T and B cells ≥45%. Thus, infusions of fully mismatched ADLs can also establish donor-specific regulation.

One DRB-Matched ADLs Expand Alloantigen-Specific Treg and Tr1 Cells

We used MHC-II tetramers to monitor circulating $CD4^+$ T cell subsets with indirect specificities for self (shared) MHC-II and mismatched donor MHC-II and MHC-I peptides. At baseline, the frequency of $CD4^+$ T cells with indirect specificities for those peptides among subsets of $CD4^+$ T cells in Cohorts B-D varied between 1.72±1.2% and 5.23±3.0%. As compared with baseline, the frequency of non-regulatory $CD4^+$ T cells with indirect specificity for self (shared) MHC-II peptides did not increase posttransplant in Cohorts B, C, and D. In contrast, a sustained increase from baseline in $CD4^+$ Treg (up to 2.43±0.35-fold) and Tr1 cells (up to 5.4±1.2-fold) with that specificity occurred in Cohort C, but not in Cohorts B and D. In Cohort D, we observed no changes posttransplant in the frequency of either non-regulatory or regulatory $CD4^+$ T cells specific for mismatched donor MHC-II peptides.

Conversely, in Cohort C, the frequency of nonregulatory $CD4^+$ T cells with specificity for mismatched donor MHC-I peptides did not change posttransplant, whereas the frequency of Treg (up to 1.93±0.0.4-fold) and Tr1 cells (up to 3.9±1.2-fold) with that specificity increased. The frequency of mismatched MHC-I-specific non-regulatory $CD4^+$ T cells increased posttransplant only in Cohort B (1.6±0.9-fold), without any changes in the corresponding subsets of Treg and Tr1 cells. Together, ADLs expanded Treg and Tr1 cells with indirect specificities for shared (self) MHC-II and mismatched MHC-I peptides in 1 MHC-II matched RM, likely contributing to induction and maintenance of tolerance.

Example 2

Absence of Biomarker Correlates with the Loss of Transplanted Islet Function

Sensitization or existence of pre-transplant donor specific immune responses has been shown to severely hamper the long-term function or induction of tolerance to transplanted solid organ or cell transplants in human and animal models. Presence of donor specific antibodies in the present preclinical model resulted in accelerated antibody mediated rejection of the transplanted islets. Serial peripheral blood samples were analyzed for the presence of Tr1 cells following the administration of the tolerance regimen in nonhuman primates with pre-existing donor-specific antibodies. Analysis of the peripheral blood samples demonstrated that the administration of the tolerance regimen results in a loss in the frequency of Tr1 cells post-transplant (on day 14) to levels below that observed in the naïve status (mean 0.59±0.24) and this absence of an increase in Tr1 cells, which is indicative of failure to induce donor-specific tolerance, correlates with the loss of islet allograft graft function. FIG. 7.

Loss of Tolerance Biomarker Precedes the Loss of Graft Function

In the present preclinical transplantation model in nonhuman primates, the administration of ADL+TIS to completely mismatched islet allograft recipients resulted in the loss of graft function at −300 days post-transplant whereas transplantation in one-DRB matched recipients resulted in indefinite survival and function of the transplanted islets (365 days). In order to test whether the loss of Tr1 cells precedes the loss of graft function in this subset of recipients, the frequency of Tr1 cells were serially analyzed by flow cytometry in peripheral blood samples collected pre- and posttransplant from the completely mismatched islet transplant recipients. Similar to the one-DRB matched group, administration of ADL+TIS resulted in a significant increase in the fold change in the frequency of Tr1 cells on day 90 (3.98±0.98), followed by a reduction at day 180 (1.98±0.75) and reached the levels observed in the naïve status on day 300 (1.19±0.1). The decrease in the frequency of circulating T cells correlated with a complete loss of graft function. These observations strongly suggest that the loss of the Tr1 cells, suggestive of the loss of the tolerance biomarker, precedes the loss of graft function by −120 days. FIG. 8.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of identifying a transplant recipient patient having long-term transplantation tolerance induced by one or more donor antigens administered under cover of transient immunotherapy, the method comprising:

(a) assaying a first blood sample from the transplant recipient patient to detect a frequency of T regulatory Type 1 (Tr1) cells in the first blood sample, wherein the first blood sample is obtained pre-tolerization, pre-transplant, and pre-initiation of administration of a transient immunotherapy to the transplant recipient patient, (b) assaying a second blood sample from the transplant recipient patient to detect a frequency of T regulatory Type 1 (Tr1) cells in the second blood sample, wherein the second blood sample is obtained at least 28 days post-tolerization, post-transplant, and post-initiation of the administration of the transient immunotherapy; and (c) identifying the transplant recipient patient as having long-term transplantation tolerance induced by the one or more donor antigens when the frequency of Tr1 cells in the second blood sample is at least 2-fold greater than the frequency of Tr1 cells in the first blood sample, wherein the pre-tolerization comprises one or more donor antigens comprised in an apoptotic donor leukocyte (ADL) infusion, wherein the transient immunotherapy comprises at least one immunosuppressant, wherein the immunosuppressant is an inhibitor of CD40:CD40L co-stimulation, an mTOR inhibitor, or a concomitant anti-inflammatory therapy targeting proinflammatory cytokines, and wherein the effect of the transient immunotherapy is for 1 day to 12 months post-administration, wherein the T regulatory Type 1 (Tr1) cells express the markers $CD49b^+$, $LAG\text{-}3^+$, and $CD4^+$, wherein the frequency of the Trl cells is a percentage of total $CD4^+$ T cells in a blood sample, and wherein the long-term transplantation tolerance is for a period of time greater than one year.

2. The method of claim 1, wherein the one or more donor antigens further comprise donor-specific transfusion (DST), nanoparticles conjugated with donor peptides or encapsulating donor peptides, and/or apoptotic recipient leukocytes conjugated with donor peptides.

3. The method of claim 1, wherein the inhibitor of CD40:CD40L co-stimulation is an antagonistic anti-CD40 antibody, a Fc-engineered (disabled, silent) anti-CD40L antibody, a Fab' anti-CD40L antibody, or a peptide interfering with CD40:CD40L co-stimulation.

4. The method of claim 1, wherein the inhibitor of CD40:CD40L co-stimulation is antagonistic anti-CD40 mAb 2C10R4.

5. The method of claim 1, wherein the mTOR inhibitor is Rapamycin.

6. The method of claim 1, wherein the transient immunotherapy comprises an anti-inflammatory agent.

7. The method of claim 6, wherein the anti-inflammatory agent is an αIL-6R and/or an sTNFR.

8. The method of claim 7, wherein the anti-inflammatory agent is tocilizumab.

9. The method of claim 7, wherein the anti-inflammatory agent is etanercept.

10. A method of treating a transplant recipient patient, the method comprising treating the transplant recipient patient identified by the method of claim 1 by ceasing to administer immunosuppressants.

11. A method, comprising:

(a) obtaining a first blood sample from a transplant recipient patient to detect a baseline frequency of Tr1 cells in the first blood sample, wherein the first blood sample is obtained pre-tolerization, pre-transplant, and pre-initiation of transient immunotherapy;

(b) obtaining a second blood sample from the transplant recipient patient to detect a frequency of Tr1 cells in the second blood sample, wherein the second blood sample is obtained at least 28 days post-tolerization, post-transplant, and post-initiation of administration of a transient immunotherapy to the transplant recipient patient;

(c) assaying the first blood sample and the second blood sample to detect levels of Tr1 cells before and after tolerization, transplantation, and initiation of the administration of the transient immunotherapy to the transplant recipient patient;

(d) identifying the transplant recipient patient as having transplantation tolerance induced by one or more donor antigens administered under cover of transient immunotherapy when the frequency of Trl cells in the second blood sample is at least 2-fold greater than the frequency of Trl cells in the first blood sample, wherein the pre-tolerization comprises one or more donor antigens comprised in an apoptotic donor leukocyte (ADL) infusion, wherein the transient immunotherapy comprises at least one immunosuppressant, wherein the immunosuppressant is an inhibitor of CD40:CD40L co-stimulation, an mTOR inhibitor, or a concomitant anti-inflammatory therapy targeting proinflammatory cytokines, and wherein the effect of the transient immunotherapy is for 1 day to 12 months post-administration, wherein the frequency of the Trl cells is a percentage of total $CD4^+$ T cells in a blood sample, and wherein the T regulatory Type 1 (Tr1) cells express the markers $CD49b^+$, $LAG\text{-}3^+$, and $CD4^+$.

12. The method of claim 11, wherein the method further comprises using one or more assays to determine that the T regulatory Type 1 (Tr1) cells have indirect specificity for at least one mismatched donor MHC class I peptide, a transcriptomic signature indicative of antigen-specific signaling, and a transcriptomic signature indicative of an activated state.

13. The method of claim 12, wherein the transcriptomic signature indicative of antigen-specific signaling comprises XBP1, SUMO2 and SH2D2.

14. The method of claim 12, wherein the transcriptomic signature indicative of an activated state comprises NDUFS4 and NDUFS5.

15. The method of claim 11, wherein at least a 2-fold increase in the frequency of Tr1 cells indicates tolerance induced by the administration of the one or more donor antigens, wherein the one or more donor antigens comprise apoptotic donor leukocytes.

16. The method of claim 11, wherein the transplant recipient patient has received two peritransplant, intravenous infusions of apoptotic donor leukocytes.

17. The method of claim 11, wherein the transplant is an allotransplant.

18. The method of claim 17, wherein the allotransplant is a solid organ allotransplant.

19. The method of claim 17, wherein the allotransplant is a cellular transplant.

* * * * *